US010228484B2

(12) United States Patent
Wang et al.

(10) Patent No.: US 10,228,484 B2
(45) Date of Patent: Mar. 12, 2019

(54) ROBUST MULTI-DIMENSIONAL INVERSION FROM WELLBORE NMR MEASUREMENTS

(71) Applicant: SCHLUMBERGER TECHNOLOGY CORPORATION, Sugar Land, TX (US)

(72) Inventors: Pu Wang, Arlington, MA (US); Vikas Jain, Sugar Land, TX (US); Lalitha Venkataramanan, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 81 days.

(21) Appl. No.: 15/337,824

(22) Filed: Oct. 28, 2016

(65) Prior Publication Data

US 2017/0123098 A1 May 4, 2017

Related U.S. Application Data

(60) Provisional application No. 62/248,655, filed on Oct. 30, 2015, provisional application No. 62/346,250, filed on Jun. 6, 2016.

(51) Int. Cl.
*G01V 3/38* (2006.01)
*G01N 24/08* (2006.01)
(Continued)

(52) U.S. Cl.
CPC ............... *G01V 3/38* (2013.01); *E21B 49/00* (2013.01); *G01N 24/081* (2013.01); *G01V 3/32* (2013.01);
(Continued)

(58) Field of Classification Search
CPC .......... G01N 24/081; G01V 3/32; G01V 3/38; G06N 7/005; G06N 99/005; E21B 47/12; E21B 49/00; G01R 33/448; G06F 17/18
(Continued)

(56) References Cited

U.S. PATENT DOCUMENTS 5,291,137 A 3/1994 Freedman
2006/0290350 A1* 12/2006 Hursan .................. G01N 24/08
324/303

(Continued)

OTHER PUBLICATIONS

Akkurt, R. et al., "NMR Logging of Natural Gas Reservoirs", The Log Analyst, 1996, 37(6), pp. 33-42.
(Continued)

*Primary Examiner* — John H Le

(57) ABSTRACT

Methods and systems for characterizing a subterranean formation using nuclear magnetic resonance (NMR) measurements are described herein. One method includes locating a downhole logging tool in a wellbore that traverses the subterranean formation, and performing NMR measurements to obtain NMR data for a region of the subterranean formation. The NMR data is processed by employing sparse Bayesian learning (SBL) to determine a multi-dimensional property distribution of the NMR data (e.g., $T_1$-$T_2$, D-$T_2$, and D-$T_1$-$T_2$ distributions). The sparse Bayesian learning can utilize Bayesian inference that involves a prior over a vector of basis coefficients governed by a set of hyperparameters, one associated with each basis coefficient, whose most probable values are iteratively estimated from the NMR data. The sparse Bayesian learning can achieve sparsity because posterior distributions of many of such basis coefficients are sharply peaked around zero.

23 Claims, 33 Drawing Sheets

(51) Int. Cl.
    *E21B 47/12*      (2012.01)
    *G06N 7/00*      (2006.01)
    *G06F 17/18*      (2006.01)
    *G01V 3/32*      (2006.01)
    *G06N 99/00*      (2019.01)
    *E21B 49/00*      (2006.01)
    *G01R 33/44*      (2006.01)

(52) U.S. Cl.
    CPC ........... *G06N 7/005* (2013.01); *G06N 99/005* (2013.01); *G01R 33/448* (2013.01)

(58) Field of Classification Search
    USPC ......... 702/6, 7, 11; 73/152.05; 324/303, 309
    See application file for complete search history.

(56) References Cited

U.S. PATENT DOCUMENTS

| | | | |
|---|---|---|---|
| 2013/0257424 A1* | 10/2013 | Holland | G01N 24/081 324/303 |
| 2016/0170065 A1* | 6/2016 | Jain | G01V 3/14 324/303 |
| 2016/0209538 A1* | 7/2016 | Wang | G01V 1/48 |

OTHER PUBLICATIONS

Allen, D. et al., "How to Use Borehole Nuclear Magnetic Resonance", 1997, Schlumberger Oilfield Review, 9(2), pp. 34-57.
Freedman, R. et al., "Fluid Characterization Using Nuclear Magnetic Resonance Logging", Petrophysics, 2004, 45 (3), 10 pages.
Freedman, R., "Advances in NMR Logging", Journal of Petroleum Technology, 2006, 58(1), pp. 60-66.
Hurlimann, M. D. et al., "Diffusion-Editing: New NMR Measurements of Saturation and Pore Geometry", presented at the 2002 Annual Meeting of the SPWLA, Oiso, Japan, 2002, 14 pages.
Kenyon, B. et al., "Nuclear Magnetic Resonance Imaging—Technology for the 21st Century", Oilfield Review, 1995, 7(3), pp. 19-33.
Kleinberg, R. L., "Well Logging, Encyclopedia of Nuclear Magnetic Resonance", vol. 8, Wiley, New York, 1996, pp. 4960-4969.
Prange, M. et al., "Quantifying uncertainty in NMR T2 spectra using Monte Carlo inversion", Journal of Magnetic Resonance, 2009, 196, pp. 54-60.
Song, Y-Q. et al., "T1-T2 Correlation Spectra Obtained Using a Fast Two-Dimensional Laplace Inversion", Journal of Magnetic Resonance, 2002, 154(2), pp. 261-268.
Venkataramanan, L. et al., "Solving Fredholm Integrals of the First Kind with Tensor Product Structure in 2 and 2.5 Dimensions", IEEE Transactions on Signal Processing, 2002, 50(5), pp. 1017-1026.

* cited by examiner

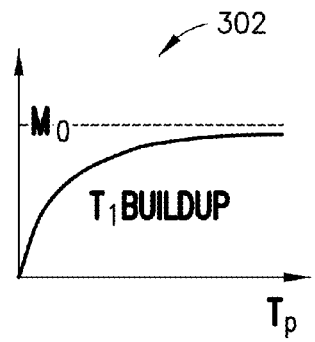
POLARIZATION PERIOD
FIG.3a
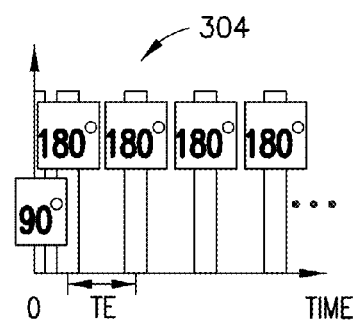
RF-PULSE SEQUENCE
FIG.3b
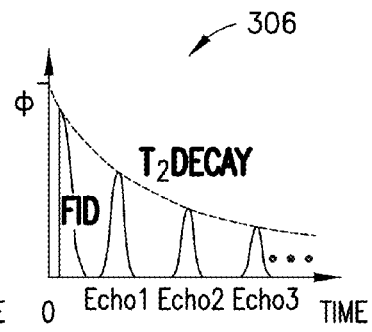
SPIN ECHOES
FIG.3c
FIG.3
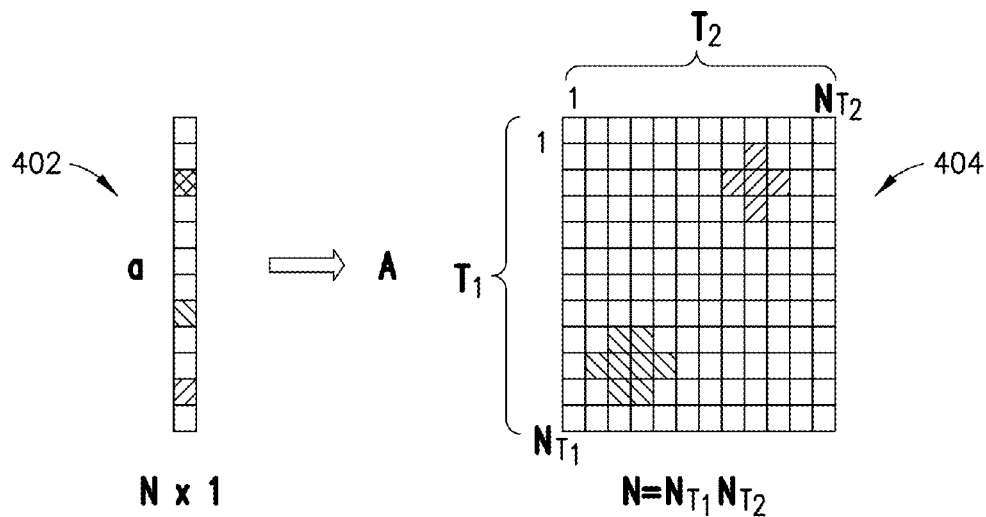
FIG.4

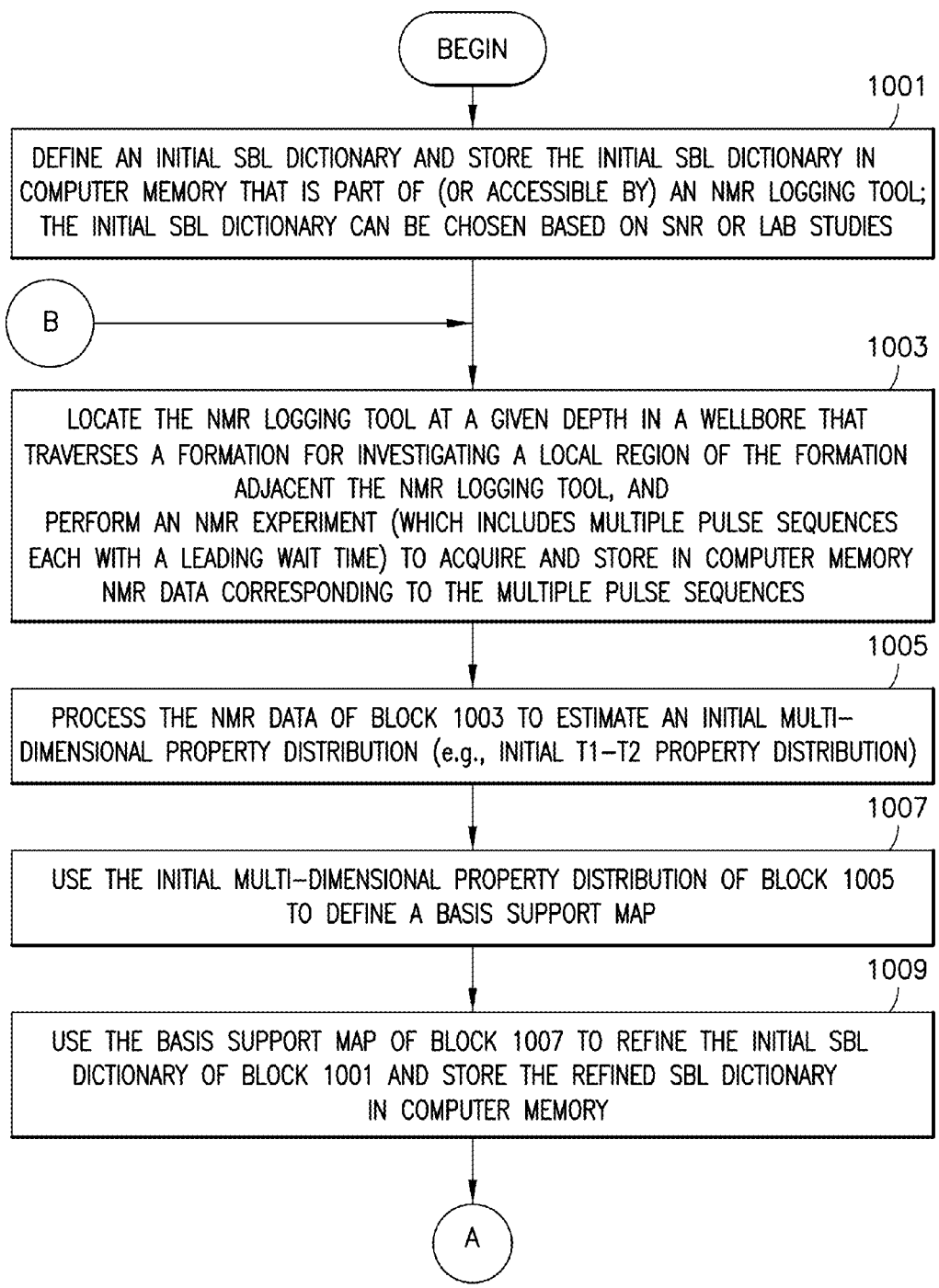
FIG.6A1

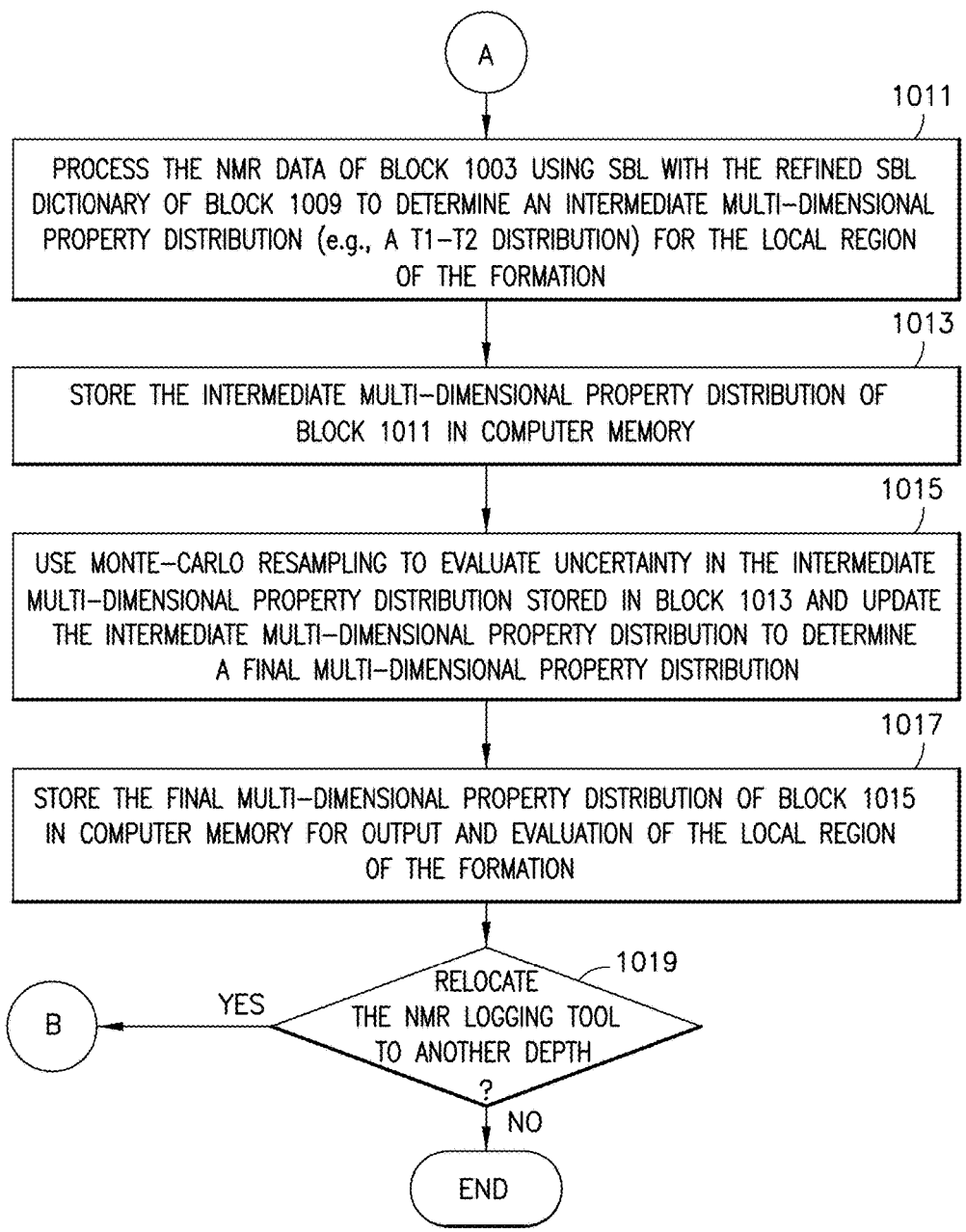
FIG.6A2

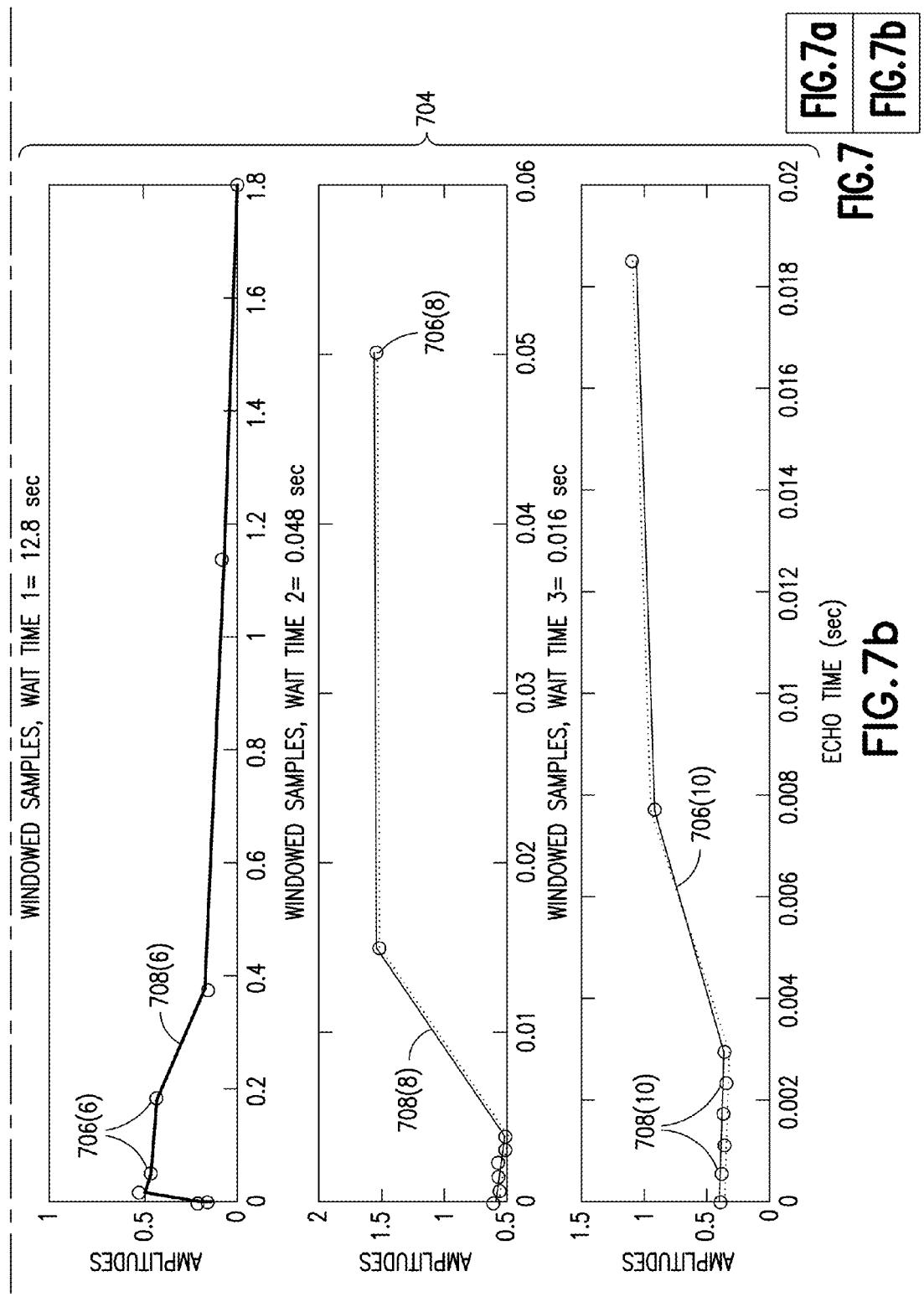

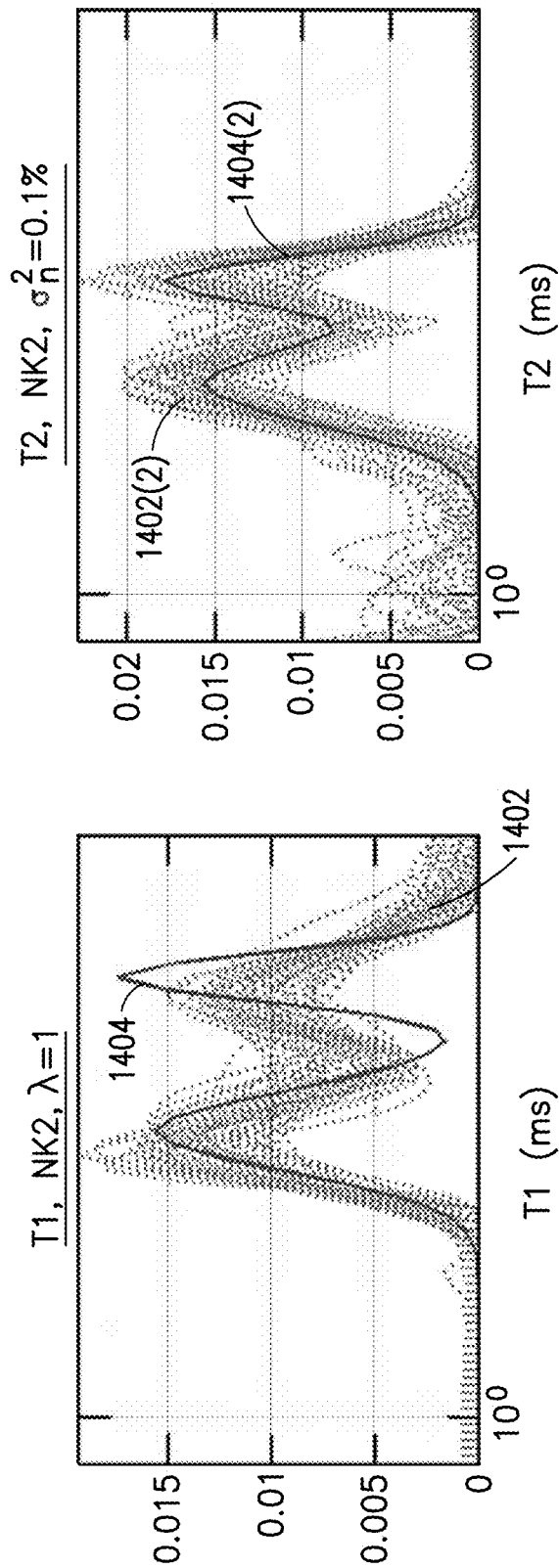

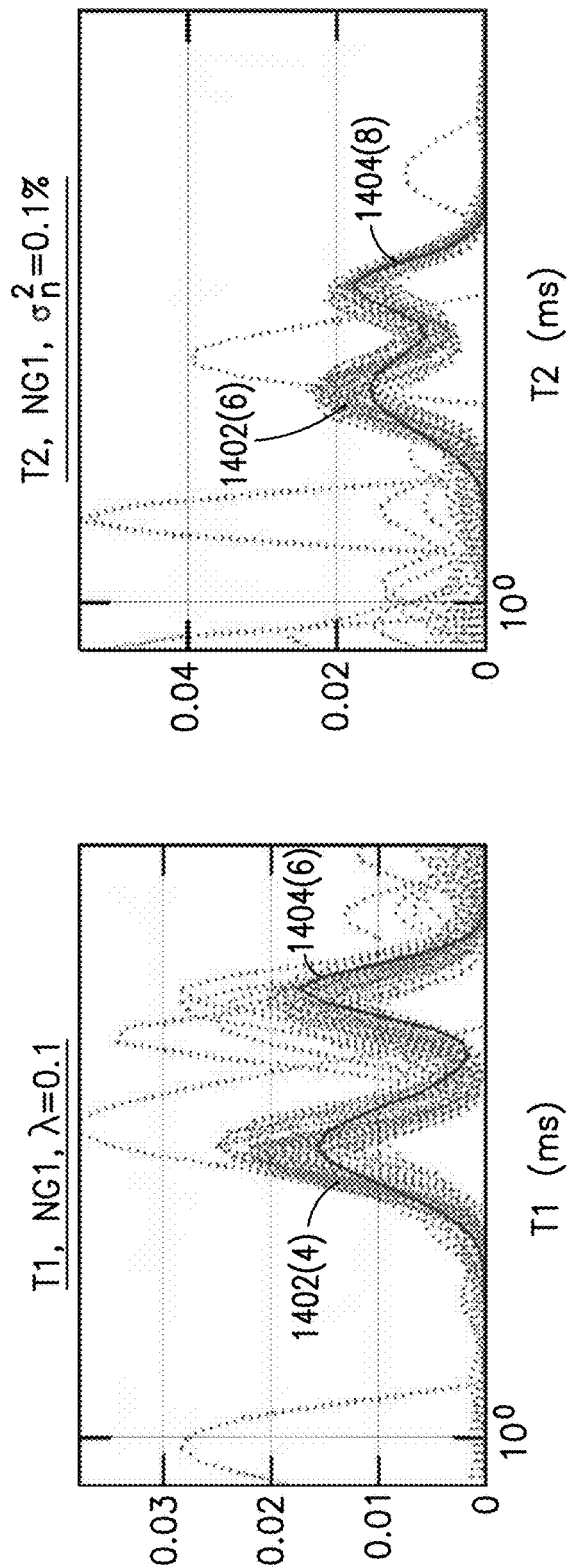

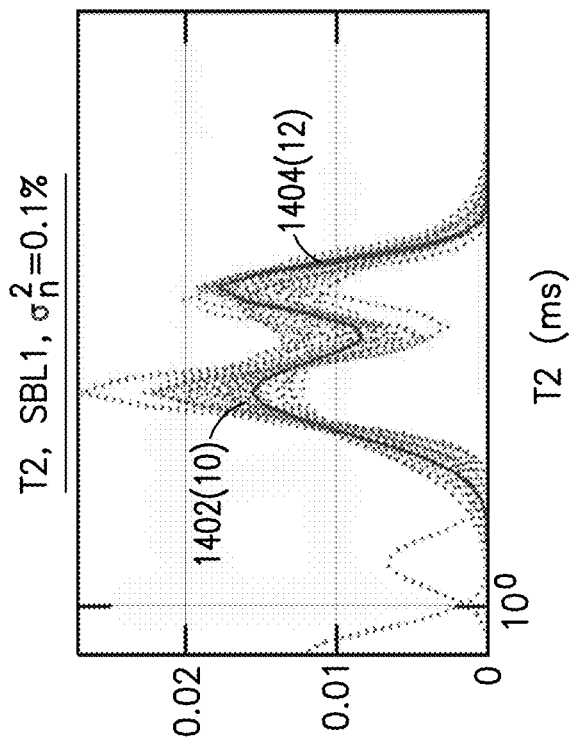
FIG. 14C2
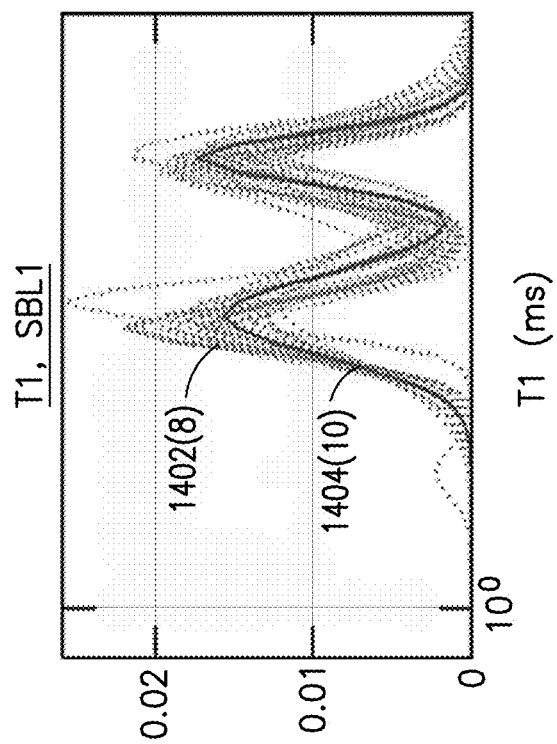
FIG. 14C1

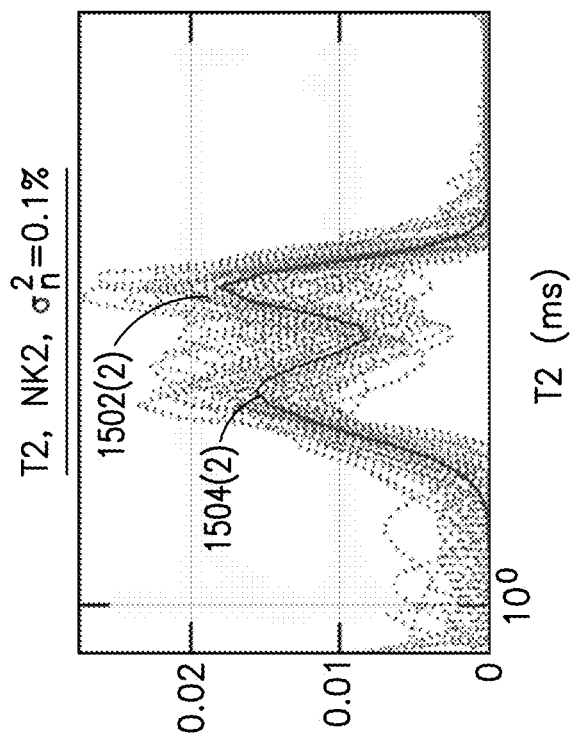
FIG.15A2
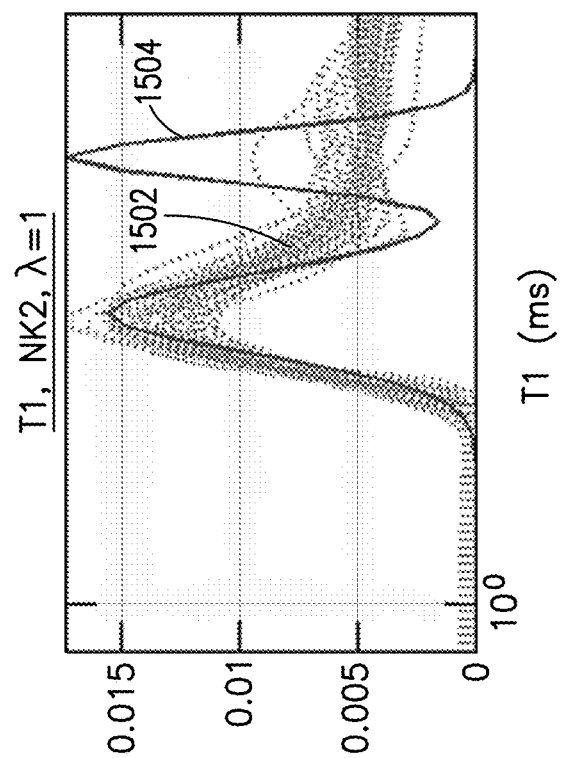
FIG.15A1

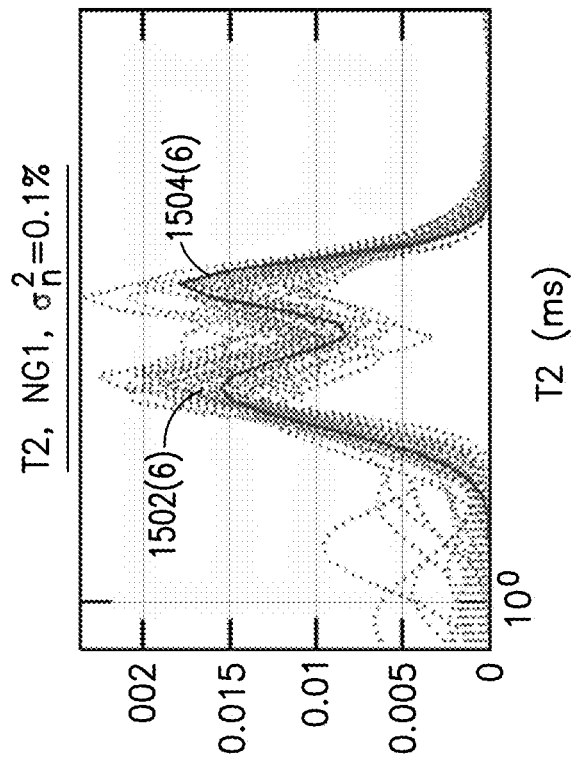
FIG. 15B2
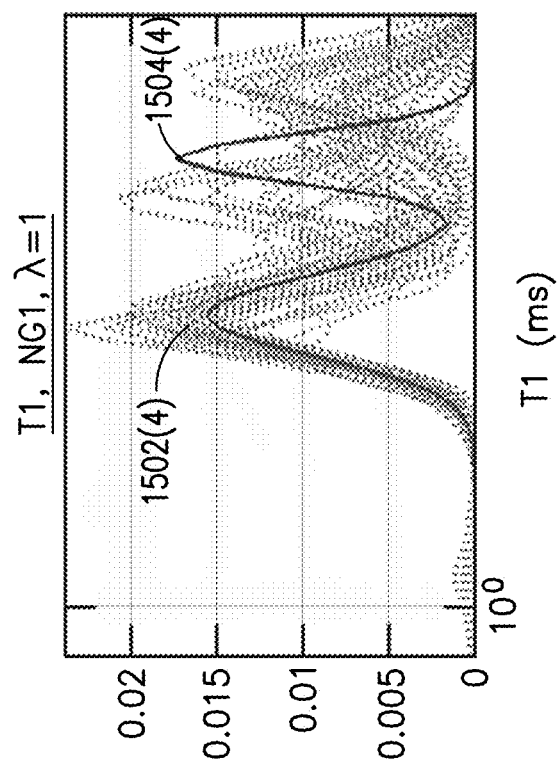
FIG. 15B1

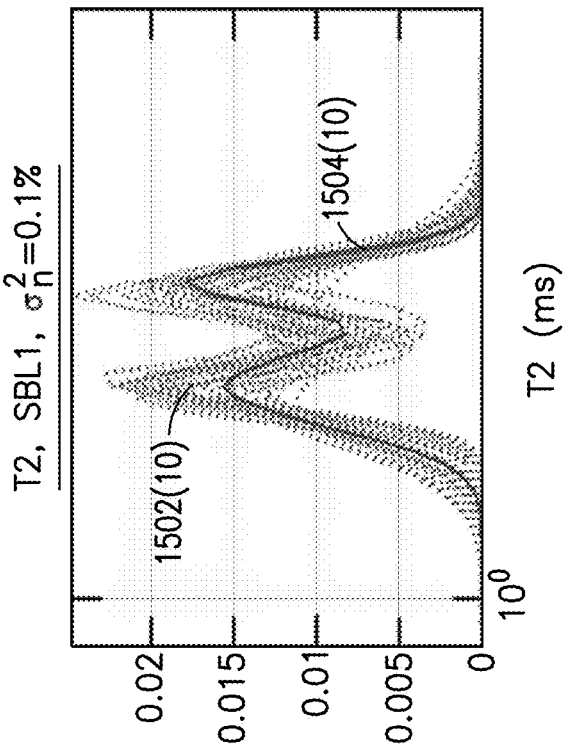
FIG.15C2
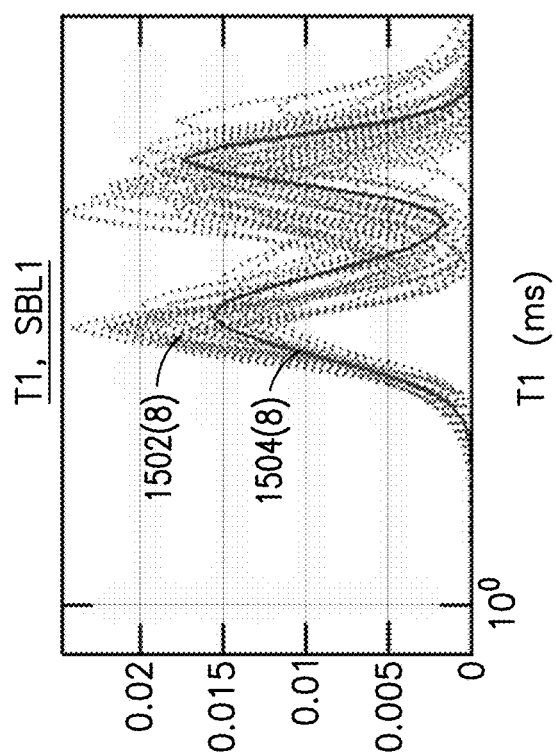
FIG.15C1

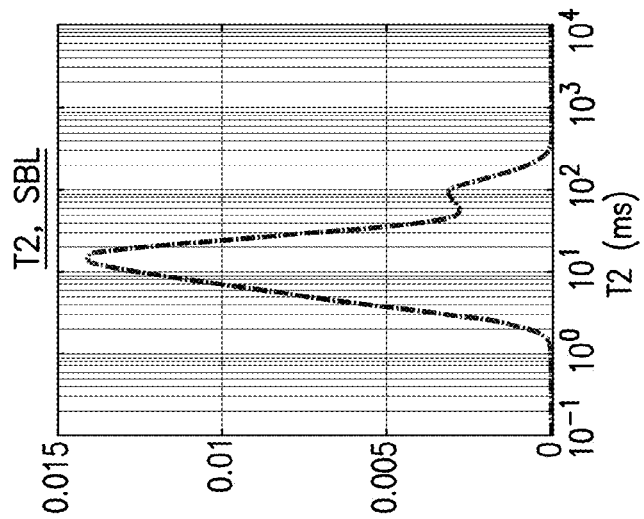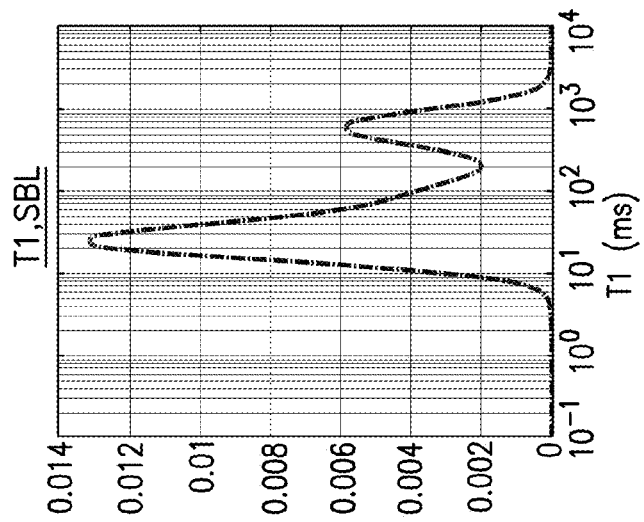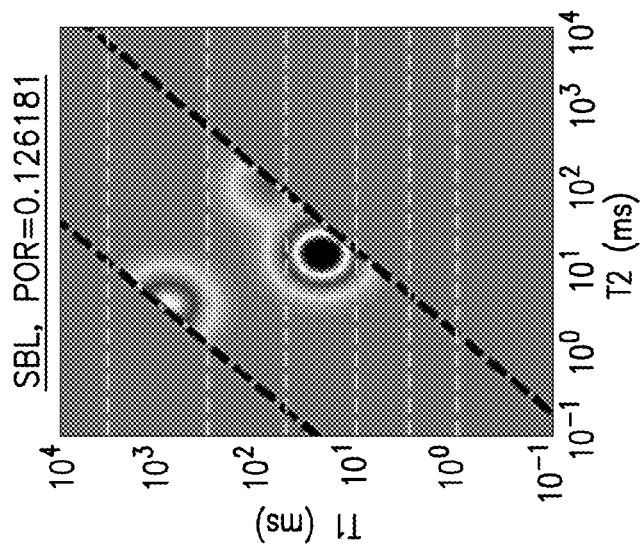

| FIG.23A |
|---|
| FIG.23B |

ROBUST MULTI-DIMENSIONAL INVERSION FROM WELLBORE NMR MEASUREMENTS

RELATED APPLICATIONS

The application claims the benefit of U.S. Application No. 62/248,655, filed on Oct. 30, 2015 and entitled "NMR Measurement Processing" and U.S. Application No. 62/346,250, filed on Jun. 6, 2016 and entitled "Robust Multi-Dimensional Inversion From NMR Measurements." Both of these applications are hereby incorporated by reference herein in their entireties.

BACKGROUND

Nuclear magnetic resonance (NMR) technologies can be useful in a wide variety of applications. For example, in the field of oilfield services, NMR logging tools can provide information regarding fluids in a formation as well as porosity of the formation. Such information can be combined with data collected using other technologies to better inform engineers as they engage in various pursuits including, for example, formation evaluation, completion engineering, geological characterization, reservoir production, etc.

NMR logging tools can be introduced into a wellbore in a variety of ways. For example, an NMR logging tool can be included in a bottom hole assembly and take measurements during a drilling operation. NMR logging tools can also be lowered into a wellbore using other technologies, such as wireline technologies. NMR tools in surface laboratories can also used to probe the pore geometry and fluids therein.

SUMMARY

A method of characterizing a subterranean formation is described that involves locating a downhole logging tool in a wellbore that traverses the subterranean formation. The tool performs a nuclear magnetic resonance (NMR) measurement and obtains NMR data for a local region of the subterranean formation adjacent the tool. The NMR data is processed by employing sparse Bayesian learning (SBL) to determine a multi-dimensional property distribution that characterizes the local region of the subterranean formation adjacent the downhole logging tool.

In some embodiments, the downhole tool obtains NMR data for different depths of investigation into the subterranean formation at a particular location in the wellbore, and the processing of the obtained NMR data can be adapted to determine multi-dimensional property distributions that characterize the different depths of investigations into the subterranean formation at the particular location in the wellbore.

In some embodiments, the downhole tool obtains NMR data for regions of the subterranean formation at different locations in the wellbore, and the processing of the obtained NMR data can be adapted to determine multi-dimensional property distributions that characterize the regions of the subterranean formation at different locations in the wellbore.

In some embodiments, the multi-dimensional property distribution can be selected from the group including T1-T2, D-T2, and D-T1-T2 distributions.

In some embodiments, the sparse Bayesian learning can utilize Bayesian inference that involves a prior over a vector of basis coefficients governed by a set of hyperparameters, one associated with each basis coefficient, whose most probable values are iteratively estimated from the NMR data. The sparse Bayesian learning can achieve sparsity because the posterior distributions of many of such basis coefficients are sharply peaked around zero.

In some embodiments, the sparse Bayesian learning can recover a basis coefficient vector from a vector representing the NMR data, a matrix representing the product of a kernel matrix and a dictionary matrix, a noise variance, and a prior variance of the basis coefficient vector. The sparse Bayesian learning can recover the basis coefficient vector by iteratively processing first and second stages, where the first stage derives a posterior distribution of the basis coefficient vector assuming the prior variance and noise variance are known, and where the second stage employs updating rules for updating the noise variance and the variance of coefficient vector. The iterative processing of the first and second stages can terminate when a stopping criterion is satisfied.

The sparse Bayesian learning can utilize a dictionary that includes a linear combination of basis elements. In one embodiment, the dictionary can be an overcomplete Gaussian dictionary.

In some embodiments, the dictionary can be a refined dictionary derived from an initial dictionary. The initial dictionary can be chosen based on signal-to-noise rate (SNR) or lab studies (e.g., from prior knowledge, available NMR data, and other measurement logs). The size of the initial dictionary can be determined or linked to SNR. The size of the initial dictionary can be determined or linked to a grid size of yet unknown multi-dimensional property distributions.

In some embodiments, the refined dictionary can be determined by deriving an estimated multi-dimensional property distribution of the NMR data, correlating the estimated multi-dimensional property distribution of the NMR data to the initial dictionary to derive a basis support map, and using the basis support map to update the initial dictionary to form the refined dictionary. The correlating can be performed over grid points of the estimated multi-dimensional property distribution of the NMR data. The basis support map can include values that indicate whether the basis of the initial dictionary corresponding to a respective grid point should be part of the refined dictionary.

In some embodiments, the NMR data is processed by sparse Bayesian learning (SBL) to determine an intermediate multi-dimensional property distribution of the NMR data. Monte-Carlo resampling can be used to evaluate uncertainty in the intermediate multidimensional property distribution and update the intermediate multi-dimensional property distribution to determine a final multidimensional property distribution. In one embodiment, the Monte-Carlo resampling can include a number of iterations each involving (i) reconstructing the NMR data from the intermediate multi-dimensional property distribution, (ii) adding artificial white Gaussian noise to the reconstructed NMR data, (iii) processing the NMR data using sparse Bayesian learning (SBL) to determine a Monte-Carlo resampled multi-dimensional property distribution, and (iv) storing the Monte-Carlo resampled multi-dimensional property distribution in computer memory. The Monte-Carlo resampling can further include combining the Monte-Carlo resampled multi-dimensional property distribution for the number of iterations to form the final multidimensional property distribution.

Any of the method embodiments discussed above can be implemented using a system with a NMR logging tool (e.g., laboratory or downhole) and a NMR processing module.

This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations can be more readily understood by reference to the following description taken in conjunction with the accompanying drawings.

FIG. 3 illustrates example NMR measurements in accordance with various embodiments of the present disclosure.

FIG. 4 illustrates an example mapping of an amplitude vector in accordance with various embodiments of the present disclosure.

FIGS. 6A1 and 6A2, collectively, is an example flowchart for a workflow employing sparse Bayesian learning (SBL) to determine a multi-dimensional property distribution of NMR data in accordance with various embodiments of the present disclosure.

FIGS. 14A1 and 14A2 illustrate example $T_1$ and $T_2$ results found by integrating an initial $T_1$-$T_2$ distribution inverted from NMR data in accordance with various embodiments of the present disclosure.

FIGS. 14B1 and 14B2 illustrate example $T_1$ and $T_2$ results found by integrating an initial $T_1$-$T_2$ distribution inverted from NMR data in accordance with various embodiments of the present disclosure.

FIGS. 14C1 and 14C2 illustrate example $T_1$ and $T_2$ results found by integrating an intermediate $T_1$-$T_2$ distribution inverted from NMR data in accordance with various embodiments of the present disclosure.

FIGS. 15A1 and 15A2 illustrate example $T_1$ and $T_2$ results found by integrating an initial $T_1$-$T_2$ distribution inverted from simulation results when a Monte-Carlo simulation is repeated with 3 wait times in accordance with various embodiments of the present disclosure.

FIGS. 15B1 and 15B2 illustrate example $T_1$ and $T_2$ results found by integrating an initial $T_1$-$T_2$ distribution inverted from simulation results when a Monte-Carlo simulation is repeated with 3 wait times in accordance with various embodiments of the present disclosure.

FIGS. 15C1 and 15C2 illustrate example $T_1$ and $T_2$ results found by integrating an intermediate $T_1$-$T_2$ distribution inverted from simulation results when a Monte-Carlo simulation is repeated with 3 wait times in accordance with various embodiments of the present disclosure.

FIG. 16A is a plot of a symmetric Gaussian basis where $n_{AT}$=1. FIG. 16B is a plot of a symmetric Gaussian basis where $n_{AT}$=2. FIG. 16C is a plot of a symmetric Gaussian basis where $n_{AT}$=3. The grid size is the same for all three plots.

FIG. 20A is a T1-T2 plot of the example intermediate T1-T2 distribution. FIG. 20B is a plot of the $T_1$ distribution that makes up the example intermediate T1-T2 distribution. FIG. 20C is a plot of the T2 distribution that makes up the example intermediate T1-T2 distribution.

FIGS. 21A, 21B and 21C are plots that illustrate an example intermediate T1-T2 distribution using SBL learning with a refined SBL dictionary. FIG. 21A is a T1-T2 plot of the example intermediate T1-T2 distribution. FIG. 21B is a plot of the $T_1$ distribution that makes up the example intermediate T1-T2 distribution. FIG. 21C is a plot of the $T_2$ distribution that makes up the example intermediate T1-$T_2$ distribution.

FIG. 24A is a T1-$T_2$ plot of the example final T1-$T_2$ distribution. FIG. 24B is a plot of the $T_1$ distribution that makes up the example final $T_1$-$T_2$ distribution. FIG. 24C is a plot of the $T_2$ distribution that makes up the example final $T_1$-$T_2$ distribution.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

Additionally, some examples discussed herein involve technologies associated with the oilfield services industry. It will be understood however that the techniques of NMR measurement processing may also be useful in a wide range of other industries outside of the oilfield services sector, including for example, mining, geological surveying, etc.

Moreover, it will also be understood that the term "optimize" as used herein can include any improvements up to and including optimization. Similarly, the term "improve" can include optimization. Other terms like "minimize" and "maximize" can also include actions reducing and increasing, respectively, various quantities and qualities.

Example Wellsite

Figure 1:
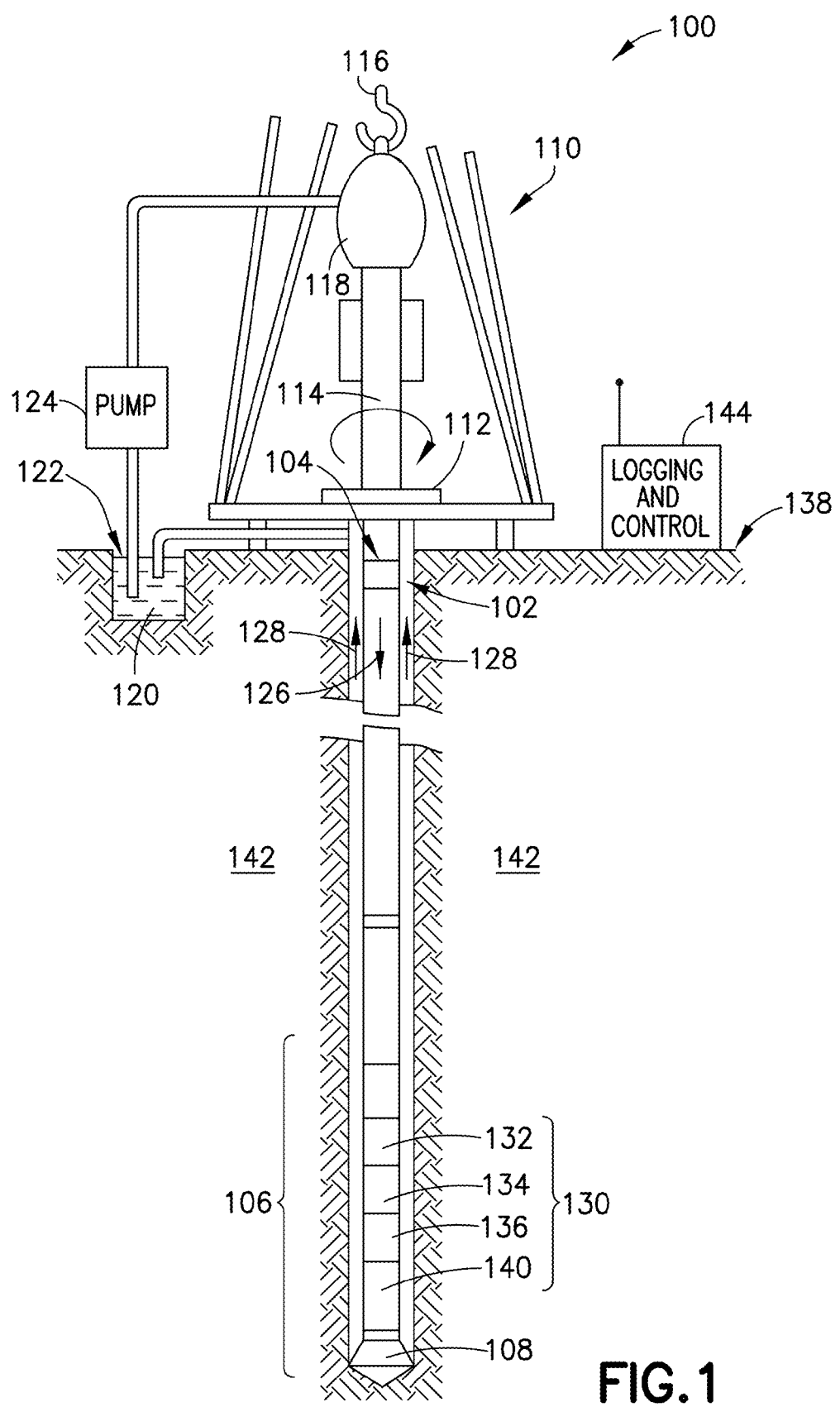
FIG. 1 illustrates an example wellsite in which embodiments of NMR measurement processing can be employed.

FIG. 1 illustrates a wellsite 100 for which embodiments of NMR measurement processing can be employed. Wellsite 100 can be onshore or offshore. In this example system, a wellbore 102 is formed in a subsurface formation by rotary drilling in a manner that is well known. Embodiments of NMR measurement processing can also be employed in association with wellsites where directional drilling is being conducted.

A drill string 104 can be suspended within the wellbore 102 and have a bottom hole assembly 106 including a drill bit 108 at its lower end. The surface system can include a platform and derrick assembly 110 positioned over the wellbore 102. The assembly 110 can include a rotary table 112, kelly 114, hook 116 and rotary swivel 118. The drill string 104 can be rotated by the rotary table 112, energized by means not shown, which engages kelly 114 at an upper end of drill string 104. Drill string 104 can be suspended from hook 116, attached to a traveling block (also not shown), through kelly 114 and a rotary swivel 118 which can permit rotation of drill string 104 relative to hook 116. As is well known, a top drive system can also be used.

In the example of this embodiment, the surface system can further include drilling fluid or mud 120 stored in a pit 122 formed at wellsite 100. A pump 124 can deliver drilling fluid 120 to an interior of drill string 104 via a port in swivel 118, causing drilling fluid 120 to flow downwardly through drill string 104 as indicated by directional arrow 126. Drilling fluid 120 can exit drill string 104 via ports in drill bit 108, and circulate upwardly through the annulus region between the outside of drill string 104 and wall of the wellbore 102, as indicated by directional arrows 128. In this well-known manner, drilling fluid 120 can lubricate drill bit 108 and carry formation cuttings up to the surface as drilling fluid 120 is returned to pit 122 for recirculation.

Bottom hole assembly 106 of the illustrated embodiment can include drill bit 108 as well as a variety of equipment 130, including a logging-while-drilling (LWD) module 132, a measuring-while-drilling (MWD) module 134, a roto-steerable system and motor, various other tools, etc.

In one possible embodiment, LWD module 132 can be housed in a special type of drill collar, as is known in the art, and can include one or more of a plurality of known types of logging tools (e.g., a nuclear magnetic resonance (NMR) system), a directional resistivity system, and/or a sonic logging system, etc.). The NMR system measures the magnetic moment of hydrogen nuclei (protons) in water and hydrocarbons. Protons have an electrical charge and their spin creates a weak magnetic moment. The NMR system employs one or more permanent magnets to create a static, magnetic-polarizing field inside the formation. The longitudinal-relaxation time, T1, describes how quickly the nuclei align, or polarize, in the static magnetic field. Full polarization of the protons in pore fluids can take up to several seconds and can be done while the NMR system of the tool is moving, but the nuclei must remain exposed to the magnetic field for the duration of the measurement. The relationship between $T_1$ and increasing pore size is direct, yet inverse, to formation fluid viscosity.

The NMR system includes transmit circuitry that supplies a series of timed radio-frequency (rf) pulses to an antenna to emit an rf field into the formation. The interaction of the rf field and static magnetic field produces a resonant region, or shell, that extends into the local region of the formation adjacent the logging tool. The depth of investigation (DOI) into the formation can vary with wellbore diameter. The rf field aligns protons of the formation that lie in the resonant region such that these protons are tilted into a plane perpendicular to the static magnetic field. These tilted protons precess around the direction of the induced magnetic field. The precessing protons create oscillating magnetic fields, which generate a measurable radio signal. However, since this signal decays rapidly, it has to be regenerated by applying a sequence of radio-frequency pulses. The precessing protons in turn generate a series of radio-signal pulses or peaks known as spin echoes that are detected by receiver circuitry of the NMR system. Signals that represent the spin echoes are converted into digital form and stored in computer memory for processing by a processing system of the NMR system (for example, the NMR measurement processing module 206 of FIG. 2) in order to determine properties of the local region of the formation adjacent the logging tool.

For example, the rate at which the proton precession decays, or loses its alignment, is called the transverse-relaxation time, $T_2$. $T_1$ and $T_2$ processes are affected predominantly by interaction between pore-fluid molecules, or bulk-relaxation characteristics, and from pore-fluid interactions with the grain surfaces of the rock matrix, also known as surface-relaxation characteristics. In addition, a magnetic-field gradient within the resonant zone can be produced by a gradient coil of the NMR system. The magnetic field gradient can induce relaxation by molecular diffusion that influences the $T_2$ processes. Such diffusion can be characterized by a diffusion constant D that can be determined from the processing of the spin echo signals acquired in the presence of the magnetic field gradient.

MWD module 134 can also be housed in a special type of drill collar, as is known in the art, and include one or more devices for measuring characteristics of the well environment, such as characteristics of the drill string and drill bit. MWD module 134 can further include an apparatus (not shown) for generating electrical power to the downhole system. This may include a mud turbine generator powered by the flow of drilling fluid 120, it being understood that other power and/or battery systems may be employed. MWD module 134 can include one or more of a variety of measuring devices known in the art including, for example, a weight-on-bit measuring device, a torque measuring device, a vibration measuring device, a shock measuring device, a stick slip measuring device, a direction measuring device, and an inclination measuring device.

It will also be understood that more than one LWD and/or MWD module can be employed. LWD module 132 can include capabilities for measuring, processing, and storing information, as well as for communicating with surface equipment.

It will also be understood that the NMR system as described herein can be embodied in a wireline logging tool that is conveyed inside a wellbore traversing a formation for determining properties of a local region of the formation adjacent the logging tool.

Various systems and methods can be used to transmit information (data and/or commands) from equipment 130 to a surface 138 of the wellsite 100. In one embodiment, information can be received by one or more sensors 140. The sensors 140 can be located in a variety of locations and can be chosen from any sensing and/or detecting technology known in the art, including those capable of measuring various types of radiation, electric or magnetic fields, including electrodes (such as stakes), magnetometers, coils, etc.

In one possible embodiment, information from equipment 130, including LWD data and/or MWD data, can be utilized for a variety of purposes including steering drill bit 108 and any tools associated therewith, characterizing a formation 142 surrounding the wellbore 102, characterizing fluids within the wellbore 102, etc.

In one possible embodiment, a logging and control system 144 can be present. Logging and control system 144 can receive and process a variety of information from a variety of sources, including equipment 130. Logging and control system 144 can also control a variety of equipment, such as equipment 130 and drill bit 108.

Logging and control system 144 can also be used with a wide variety of oilfield applications, including logging while drilling, artificial lift, measuring while drilling, wireline, etc. Also, logging and control system 144 can be located at surface 138, below surface 138, proximate to the wellbore 102, remote from wellbore 102, or any combination thereof.

For example, in one possible embodiment, information received by equipment 130 and/or sensors 140 can be processed by logging and control system 144 at one or more locations, including any configuration known in the art, such as in one or more handheld devices proximate and/or remote from the wellsite 100, at a computer located at a remote command center, etc. In one possible embodiment, logging and control system 144 can be used to perform various aspects of the NMR measurement processing as described herein.

Example Computing Device

Figure 2:
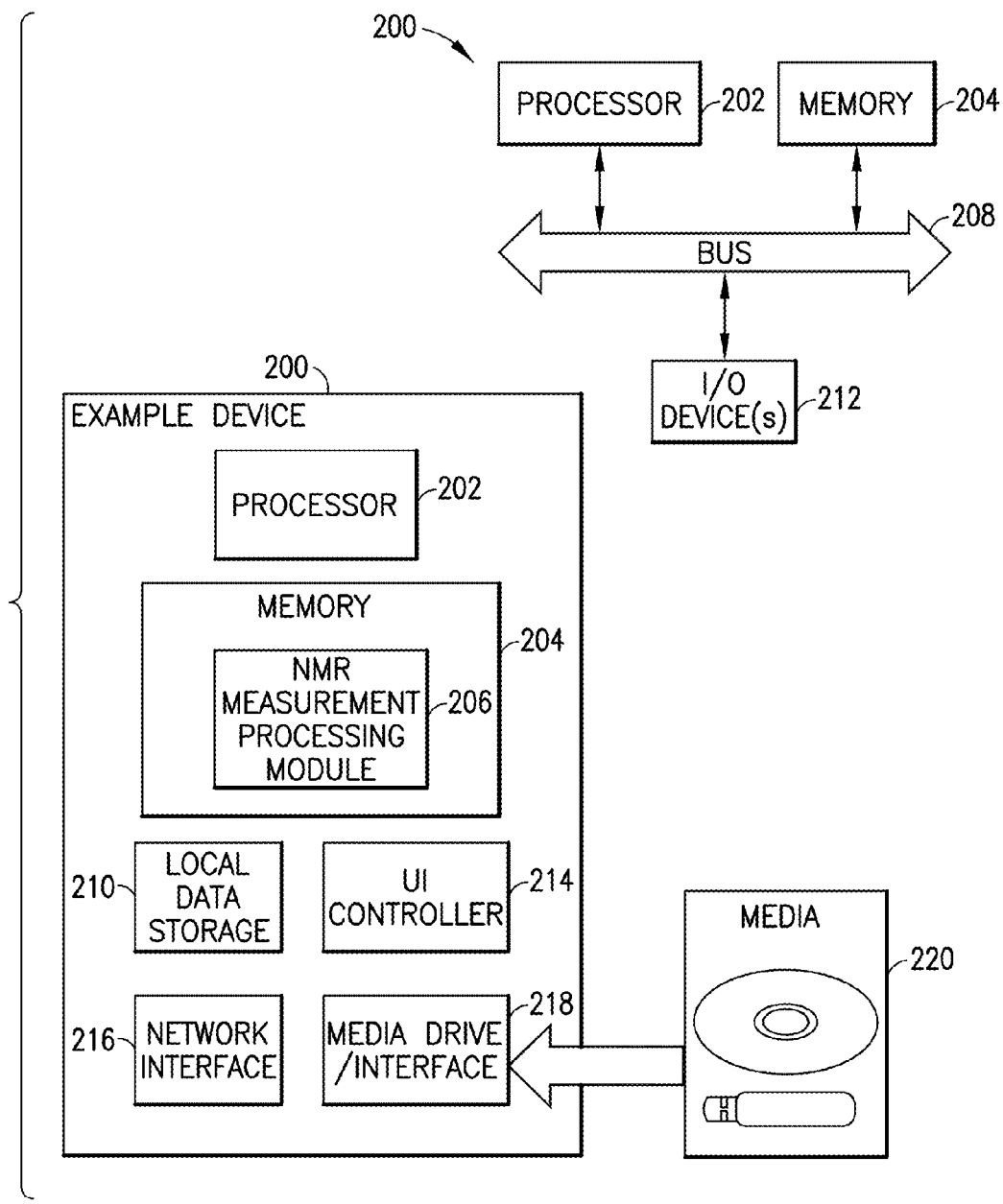
FIG. 2 illustrates an example computing device that can be used in accordance with various embodiments of the present disclosure.

FIG. 2 illustrates an example device 200 (including a processor 202 and computer memory 204) that embodies an NMR measurement processing module 206 configured to implement various operations of the NMR measurement processing discussed in this disclosure. Computer memory 204 can include one or more forms of volatile data storage media such as random access memory (RAM), and/or one or more forms of nonvolatile storage media (such as read-only memory (ROM), flash memory, and so forth).

Device 200 is one example of a computing device or programmable device, and is not intended to suggest any limitation as to scope of use or functionality of device 200 and/or its possible architectures. For example, device 200 can comprise one or more computing devices, programmable logic controllers (PLCs), etc.

Further, device 200 should not be interpreted as having any dependency relating to one or a combination of components illustrated in device 200. For example, device 200 may include one or more of a computer, such as a laptop computer, a desktop computer, a mainframe computer, etc., or any combination or accumulation thereof.

Device 200 can also include a bus 208 configured to allow various components and devices, such as processors 202, memory 204, and local data storage 210, among other components, to communicate with each other.

Bus 208 can include one or more of any of several types of bus structures, including a memory bus or memory controller, a peripheral bus, an accelerated graphics port, and a processor or local bus using any of a variety of bus architectures. Bus 208 can also include wired and/or wireless buses.

Local data storage 210 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 212 may also communicate via a user interface (UI) controller 214, which may connect with I/O device(s) 212 either directly or through bus 208.

In one possible embodiment, a network interface 216 may communicate outside of device 200 via a connected network, and in some implementations may communicate with hardware, such as equipment 130, one or more sensors 140, etc.

A media drive/interface 218 can accept removable tangible media 220, such as flash drives, optical disks, removable hard drives, software products, etc. In one possible embodiment, logic, computing instructions, and/or software programs comprising elements of NMR measurement processing module 206 may reside on removable media 220 readable by media drive/interface 218.

In one possible embodiment, input/output device(s) 212 can allow a user to enter commands and information to device 200, and also allow information to be presented to the user and/or other components or devices. Examples of input device(s) 212 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of NMR measurement processing module 206 may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

In one possible embodiment, device 200, or a plurality thereof, can be employed at wellsite 100. This can include, for example, in various equipment 130, in logging and control system 144, etc.

Example System(s) and/or Technique(s)

In one possible embodiment, various techniques and technologies associated with NMR measurement processing can be used to reformulate a multi-dimensional NMR inversion problem into a non-linear system with an overcomplete dictionary and treat multi-dimensional amplitudes as random parameters. A workflow can then be derived by using the framework of, for example, sparse Bayesian learning (SBL) which may yield a solution with a few non-zero values. SBL is a computational method for obtaining a sparse representation of input data in the form of a linear combination of basis elements as well as the basis elements themselves. These basis elements compose a dictionary. The sparse representation of the input data is solved for using Bayesian inference that involves a prior over a vector b of basis coefficients or weights governed by a set of hyperparameters, one associated with each basis coefficient, whose most probable values are iteratively estimated from the input data. Sparsity is achieved because in practice the posterior distributions of many of such basis coefficients are sharply peaked around zero.

In another possible embodiment, a workflow can jointly invert a multi-dimensional property distribution (such as $T_1$-$T_2$, D-$T_2$, and D-$T_1$-$T_2$) from wellbore nuclear magnetic resonance (NMR) measurements by using sparse Bayesian learning (SBL). The multi-dimensional property distribution can characterize the local region (or volume) of the subterranean formation that is investigated by the wellbore nuclear magnetic resonance (NMR) measurements with the downhole NMR tool located at a particular depth or location within a well. The workflow can be adapted to acquire and process wellbore nuclear magnetic resonance (NMR) measurements at different depths of investigation with the downhole NMR tool located at a particular depth or location within a well in order to characterize the different depths of investigation into the subterranean formation at the particular depth or location within the well. In this case, the wellbore nuclear magnetic resonance (NMR) measurements can be carried out over several RF frequencies in order to measure (image) multiple sample volumes at different depths of investigation with the downhole NMR tool located at the particular depth or location within the well. The workflow can also be adapted to acquire and process wellbore nuclear magnetic resonance (NMR) measurements at different depth or locations in the well in order to characterize regions (or volumes) of the subterranean formation at different depths or locations in the well. Such SBL-based multi-dimensional inversion can be used to invert Carr-Purcell-Meiboom-Gill (CPMG) sequences with a few wait times by automatically exploiting sparsity in the solution space, which can be characterized by an overcomplete dictionary. In one possible embodiment, the combination of automated inversion and a few wait times can potentially save time during an NMR logging process.

In one possible embodiment, an overcomplete dictionary can be formed from a structural matrix, which can capture the local cluster feature of a multi-dimensional property distribution such as $T_1$-$T_2$, D-$T_2$, and D-$T_1$-$T_2$ (e.g., a two-dimensional Gaussian support matrix for the $T_1$-$T_2$ distribution) (see Eqns. (5) and (6) for details). Other possible choices for the structural matrix include a two-dimensional ellipse matrix, a two-dimensional wavelet matrix, etc.

In other possible embodiments, aspects of NMR measurement processing can be applied to multi-dimensional NMR inversion including, for example, simultaneous inversion of NMR measurements acquired at multiple-depths of investigations, at multiple frequencies, etc. In one possible embodiment, NMR measurement processing can be used with any form of NMR acquisition sequence since it utilizes an expected sparsity of NMR's solution space. In one possible embodiment, sparsity can be used to potentially enable fast NMR logging and high resolution in the inverted multi-dimensional distribution with potentially reduced waiting times at each logging depth.

In one possible embodiment, NMR measurement processing can be used to create one or more multi-dimensional property distributions with wellbore NMR tools by acquiring less NMR measurements than might be collected using conventional NMR logging techniques at each logging depth. By using less NMR measurements, a workflow can utilize the sparsity of active responses in the multi-dimensional relaxation distribution. In one possible embodiment, the workflow can also treat a multi-dimensional property distribution as a random unknown, and recover it using, for example, Sparse Bayesian Learning (SBL).

FIG. 3 illustrates example NMR measurements that can be part of the NMR measurement processing. As illustrated, the NMR measurements include (a) a wait time (WT) 302 (also referred to as a "polarization period") to build up magnetization toward the equilibrium value M0, (b) an RF pulse sequence 304 that follows the wait time 302; for example, the RF pulse sequence 304 can be a Carr-Purcell-Meiboom-Gill (CPMG) sequence that includes a 90° RF pulse followed by a train of 180° pulses, etc., and (c) spin-echo signals 306 that are induced by the RF pulse sequence.

In one possible embodiment, during well-logging, pore-size distributions in rocks and component distributions in hydrocarbons can give rise to distributions of longitudinal relaxation time ($T_1$), transverse relaxation time ($T_2$), and diffusion coefficients D observed with nuclear magnetic resonance (NMR) measurements. In one possible embodiment, estimation of these property distributions from the NMR measurement data can play a role in the inference of various in situ petro-physical and fluid properties in formation 142.

In one possible embodiment, a two-stage acquisition scheme can be employed to establish NMR measurements. For example, the first stage can include creating a net magnetization of reservoir fluids in the resonant zone adjacent the logging tool. With the logging tool located at a depth or position in the wellbore 102, the magnetic-field vector, $B_0$, of the permanent magnet of the NMR system of the logging tool can polarize the hydrogen nuclei in the reservoir fluids creating a net magnetization. The magnetization can be along the direction of $B_0$, which can be called the longitudinal direction. During the wait time (WT) of an NMR measurement, the magnetization can grow exponentially toward its equilibrium value; see, for example, FIG. 3A. In one possible embodiment, the time constant that characterizes the exponential buildup of the magnetization can be the longitudinal relaxation time, which is referred to as $T_1$. In reservoir rocks, a distribution of $T_1$ values can describe the magnetization process as the $T_1$ distribution reflects the complex compositions of hydrocarbons and the distribution of oil and water in different pore sizes in sedimentary rocks in formation 142.

In one possible embodiment, the second stage can follow the wait time (WT) and supply the RF pulse sequence 304 to the antenna of the NMR system. With the logging tool located at a depth or position in the wellbore 102, the supply of the RF pulse sequence 304 to the antenna emits an rf field into the formation. For example, the RF pulse sequence 304 can be a CPMG sequence that includes an initial 90° pulse followed by a series of evenly spaced 180° pulses as shown in FIG. 3B. The initial pulse is a 90° pulse because it rotates the magnetization vector, which is initially parallel to $B_0$, into the transverse plane perpendicular to $B_0$. Each 180° pulse refocuses the magnetic moments of the hydrogen nuclei to form a coherent spin-echo signal that is received by the antenna and receiver circuitry of the NMR system of the logging tool. The spin echo signals can be recorded between each pair of 180° pulses as shown in FIG. 3C. In one possible aspect, the envelope of the spin-echo signal can decay exponentially with a characteristic time constant, $T_2$, known as the transverse or spin-spin relaxation (i.e., decay) time.

The wait time (WT) is the time between (i) application of the static magnetic field to the area-of-interest (e.g., in the formation) to (ii) application of the first RF pulse of the RF pulse sequence 304 (e.g., the initial 90° pulse of the CPMG sequence).

Conventional NMR data processing can measure the $T_2$ distribution from the spin-echo signal with a single wait time (WT). Approaches can include, for example, the non-negative Tikhonov regularized least square method and the Monte-Carlo Bayesian sampler method for one-dimensional $T_2$ inversion. Continued advances in wellbore NMR data acquisition and processing have triggered interest in deriving multi-dimensional property distributions (such as $T_1$-$T_2$, D-$T_2$, and D-$T_1$-$T_2$ distributions) which facilitate identification of fluids present in a reservoir. The multi-dimensional property distribution can be used for accurate fluid analysis of reservoirs invaded with oil-based drilling-mud filtrate. In one possible aspect, the multi-dimensional inversions may not rely on empirical models, which may be desirable when attempting to identify and characterize several miscible fluids. In one possible aspect, a multi-dimensional inversion can be achieved using, for example, the multi-dimensional non-negative Tikhonov regularized least square method and the $L_1$-minimization method. Both methods involve the selection of a regularization parameter which controls the trade-off between the fitting residuals and the penalty term. Such selection may be addressed using, for example, the L-curve method, the cross-validation method, and/or the Kolmogorov-Smirnov procedure. For each of these selection choices, multiple start-over runs of the entire method may be used, which can increase a corresponding computational burden.

In one possible embodiment, an automatic workflow can be used to estimate multi-dimensional property distributions from NMR measurements without selecting a regularization parameter and/or with minimal human intervention. In one possible embodiment, a multi-dimensional NMR inversion problem can be reformulated into a non-linear system with an overcomplete dictionary, where multi-dimensional amplitudes can be treated as random parameters. Such an automatic workflow can be derived, for example, using the framework of Sparse Bayesian Learning (SBL) which can facilitate the solution with a few non-zero values.

In one possible embodiment, a multi-dimensional NMR inversion can be formulated in a non-linear overcomplete system.

In another possible embodiment, a multi-dimensional NMR inversion can be logically partitioned in two stages. In the first stage, multi-dimensional amplitudes are estimated provided that prior and noise variances are known. In the second stage, the prior and noise variances are updated. In the following, an example of the general multi-dimensional inversion using the NMR $T_1$-$T_2$ inversion will be explained. It should be noted, however, that the described algorithm can be designed for a general multi-dimensional inversion including $T_1$-$T_2$, D-$T_2$, and D-$T_1$-$T_2$ inversions.

Example Problem Formulation

In one possible embodiment, a NMR measurement can relate to the probability density of $T_1$ and $T_2$ via the following signal model $$y_i = \Phi_i a + v_i, \quad i=1,2,\ldots,I \tag{1}$$

where $y_i = [y_i(1)\ y_i(2)\ \ldots\ y_i(M_i)]^T$ is the spin-echo signal vector of length $M_i$ corresponding to the i-th WT, with $[\bullet]^T$ denoting the matrix/vector transpose operator, $\Phi_i = [\Phi_{i,1}\ \Phi_{i,2}\ \ldots\ \Phi_{i,N}]$ is the kernel matrix of size $M_i \times N$, $a = [a(1)\ a(2)\ \ldots\ a(N)]^T$ is the non-negative amplitude vector, and $v_i$ is the noise vector of length $M_i$.

Each column of the kernel matrix $\Phi_i$ can be specified by:

$$\Phi_{i,n} = \left(1 - e^{-\frac{WT_i}{T_1(n)}}\right)\left[e^{-\frac{\Delta t_i}{T_2(n)}}\ e^{-\frac{2\Delta t_i}{T_2(n)}}\ \ldots\ e^{-\frac{M_i \Delta t_i}{T_2(n)}}\right]^T \tag{2}$$

where $WT_i$ denotes the i-th wait time, $\Delta t_i$ denotes the i-th echo spacing, $T_1(n)$ denotes the n-th $T_1$ grid value, and $T_2(n)$ denotes the n-th $T_2$ grid value, with the pair of $\{T_1(n), T_2(n)\}$ corresponding to element $a(n)$ of the amplitude vector a.

By stacking the spin-echo signal vectors $y_i$ for I wait times, the overall signal model can be written as $$y = \Phi a + v \tag{3}$$

where $$y = \begin{bmatrix} y_1 \\ y_2 \\ \vdots \\ y_I \end{bmatrix}, \Phi = \begin{bmatrix} \Phi_1 \\ \Phi_2 \\ \vdots \\ \Phi_I \end{bmatrix}, \text{ and } v = \begin{bmatrix} v_1 \\ v_2 \\ \vdots \\ v_I \end{bmatrix}$$

In one possible embodiment, if the amplitude vector a can be mapped back to the two-dimensional $T_1$-$T_2$ distribution A, as follows:

$$A = \text{reshape}(a, N_{T_1}, N_{T_2}) \in \Re^{N_{T_1} \times N_{T_2}} \tag{4}$$

For example, if the MATLAB notation of reshape is followed, one may be able to find the local cluster feature of the inverted $T_1$-$T_2$ distribution. FIG. 4 illustrates an example mapping of the amplitude vector a 402 of length N into the $T_1$-$T_2$ distribution A 404 of size $NT_1 \times NT_2$ and the local cluster feature of A.

To utilize the local cluster feature of the solution space, the cluster feature can be incorporated with an overcomplete two-dimensional Gaussian dictionary. For example, the two dimensional $T_1$-$T_2$ distribution A can be represented by a linear combination of two-dimensional Gaussian functions over the two-dimensional $T_1$-$T_2$ grids with different concentrations (variances along the $T_1$ and $T_2$ directions). In one possible embodiment, for each grid in the $T_1$-$T_2$ distribution:

$$A(n_1, n_2) = \sum_{l=1}^{L} b(l) e^{-\left\{\frac{(n_1-T_1(l))^2}{2\sigma_{1,l}^2} + \frac{(n_2-T_2(l))^2}{2\sigma_{2,l}^2}\right\}}, \quad (5)$$

$$n_1 \in [1, N_{T_1}], n_2 \in [1, N_{T_2}]$$

where b(l) is the weight for the l-th Gaussian basis function centered at $[T_1(l), T_2(l)]$ with variances $\sigma_{1,l}^2$ and $\sigma_{2,l}^2$, and L is the number of Gaussian basis functions.

In one possible embodiment, this can be equivalent to expressing the distribution A as:

$$A = \sum_{l=1}^{L} b(l) G_l \quad (6)$$

where $$G_l \in \Re^{N_{T_1} \times N_{T_2}}$$

is given as:

$$G_l = \begin{bmatrix} e^{-\left\{\frac{(1-T_1(l))^2}{2\sigma_{1,l}^2} + \frac{(1-T_2(l))^2}{2\sigma_{2,l}^2}\right\}} & e^{-\left\{\frac{(1-T_1(l))^2}{2\sigma_{1,l}^2} + \frac{(2-T_2(l))^2}{2\sigma_{2,l}^2}\right\}} & \cdots & e^{-\left\{\frac{(1-T_1(l))^2}{2\sigma_{1,l}^2} + \frac{(N_{T_2}-T_2(l))^2}{2\sigma_{2,l}^2}\right\}} \\ e^{-\left\{\frac{(2-T_1(l))^2}{2\sigma_{1,l}^2} + \frac{(1-T_2(l))^2}{2\sigma_{2,l}^2}\right\}} & e^{-\left\{\frac{(2-T_1(l))^2}{2\sigma_{1,l}^2} + \frac{(2-T_2(l))^2}{2\sigma_{2,l}^2}\right\}} & \cdots & e^{-\left\{\frac{(2-T_1(l))^2}{2\sigma_{1,l}^2} + \frac{(N_{T_2}-T_2(l))^2}{2\sigma_{2,l}^2}\right\}} \\ \vdots & \vdots & \ddots & \vdots \\ e^{-\left\{\frac{(N_{T_1}-T_1(l))^2}{2\sigma_{1,l}^2} + \frac{(1-T_2(l))^2}{2\sigma_{2,l}^2}\right\}} & e^{-\left\{\frac{(N_{T_1}-T_1(l))^2}{2\sigma_{1,l}^2} + \frac{(2-T_2(l))^2}{2\sigma_{2,l}^2}\right\}} & \cdots & e^{-\left\{\frac{(N_{T_1}-T_1(l))^2}{2\sigma_{1,l}^2} + \frac{(N_{T_2}-T_2(l))^2}{2\sigma_{2,l}^2}\right\}} \end{bmatrix}$$

By stacking the columns of A on top of each other, the amplitude vector a can be represented as:

$$a = vec\{A\} = \sum_{l=1}^{L} b(l) vec\{G_l\} = Gb \quad (7)$$

where $$G \in \Re^{N_{T_1} N_{T_2} \times L}$$

is the Gaussian dictionary with L columns, each formed by the vectorized $G_l$, and the basis coefficient vector b is given by $b=[b_1\ b_2\ \ldots\ b_L]^T$.

Eqns. (3) and (7) can be combined to form the overall signal model with the local Gaussian cluster feature given by:

$$y = \Phi G b + v = \Gamma b + v \quad (8)$$

where $\Gamma$ is the matrix representing the product of the kernel matrix $\Phi$ and the Gaussian dictionary matrix G.

Given the signal model of Eqn. (8), the basis coefficient vector b can be estimated/recovered given the measurement vector y via $y=\Gamma b$ of Eqn. (8). Once b is estimated, the amplitude vector a can be recovered via $a=Gb$ of Eqn. (7) and, then, the two dimensional $T_1$-$T_2$ distribution A can be recovered via Eqn. (4).

Example Multi-Dimensional Property Inversion of NMR Data Via Sparse Bayesian Learning In one possible embodiment, an automatic workflow can employ a sparse Bayesian learning (SBL) framework to estimate the basis coefficient vector b from the measurement vector y. The SBL framework can assume the basis coefficient vector b as a random Gaussian vector as follows:

$$b \sim N(0, \Lambda) \quad (9)$$

where the covariance matrix is $\Lambda = \text{diag}[\lambda_1, \lambda_2, \ldots, \lambda_L]$. The SBL framework can also assume the noise v is also Gaussian distributed as follows:

$$v \sim N(0, \sigma^2 I_M) \quad (10)$$

where $I_M$ can be the identity matrix of size M.

Figure 5:
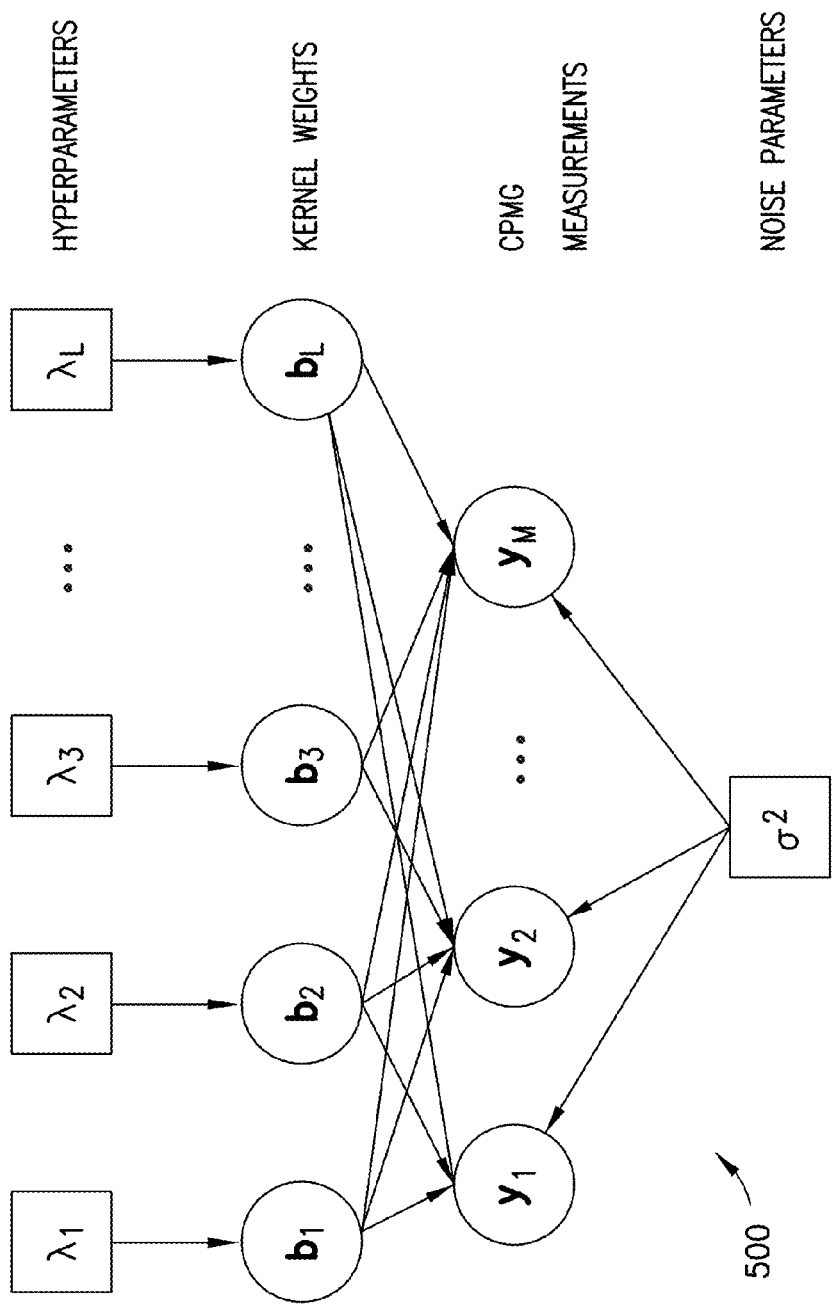
FIG. 5 illustrates an example representation of the signal model assumed for sparse Bayesian learning in accordance with various embodiments of the present disclosure.

FIG. 5 illustrates an example representation of the signal model assumed for the sparse Bayesian learning framework. As illustrated, the overall signal structure can be represented by a graph model 500.

In one possible embodiment, the automatic workflow employing a sparse Bayesian learning (SBL) framework can be described in two stages. In the first stage, assuming the prior and noise variances are known, the posterior distribution of the basis coefficient vector b can be derived given the measurement vector y:

$$b|y; \{\lambda_i\}_{i=1}^{L}, \sigma^2 \sim N(u, \Sigma_b) \quad (11)$$

where the posterior mean is given by:

$$u = \sigma^{-2} \Sigma_b \Gamma^T y \quad (12)$$

and the posterior covariance matrix is given by:

$$\Sigma_b = (\sigma^{-2} \Gamma^T \Gamma + \Lambda^{-1})^{-1} \quad (13)$$

Then the Bayesian maximum a posterior (MAP) estimate of b (denoted $\hat{b}$), or, equivalently, the Bayesian minimum mean square error (MMSE) estimate, can be given by the posterior mean:

$$\hat{b} = u = \sigma^{-2} \Sigma_b \Gamma^T y \quad (14)$$

In one possible embodiment, a hard-threshold operator can be used to incorporate a non-negative constraint for $\hat{b}$ as follows:

$$\hat{b} = u \odot 1(u \geq 0) \quad (15)$$

where $\odot$ indicates the dot product, or scalar product, between two vectors of the same length, and 1(•) is the indicator function, which is 1 if the augment is true and 0 otherwise.

From Eqn. (15), it can be noted that the Bayesian estimate $\hat{b}$ can be a function of the noise variance $\sigma^{-2}$ and the prior variance $\{\lambda_l\}_{l=1}^{L}$ via $\Sigma_b$.

In one possible embodiment, the second stage derives an update rule for the noise variance $\sigma^{-2}$ and the prior variance $\{\lambda_l\}_{l=1}^{L}$ via $\Sigma_b$. To achieve this, the marginal distribution of the measurement vector y can be derived by integrating the likelihood function over the prior distribution of the basis coefficient vector b as follows:

$$y; \{\lambda_l\}_{l=1}^{L}, \sigma^2 \sim N(0, \Sigma_y) \quad (16)$$

where the marginal covariance matrix can be given as:

$$\Sigma_y = \sigma^2 I_M + \Gamma \Lambda \Gamma^T \quad (17)$$

Then, in one possible embodiment, the marginal maximum likelihood (ML) estimate of the noise variance $\sigma^{-2}$ and the prior variance $\{\lambda_l\}_{l=1}^{L}$ can be derived by taking the derivatives of the marginal likelihood function of Eqn. (16) with respect to the noise variance $\sigma^{-2}$ and the prior variance $\{\lambda_l\}_{l=1}^{L}$ and equating such derivative to zero. In one possible embodiment, a direct maximization yields no closed-form solutions for the marginal ML estimation. In the following, two strategies can be considered for such updates: 1) the Fixed-Point (FP) algorithm; and 2) the Expectation-Maximization (EM) algorithm.

For the FP algorithm, the updating rules for the noise variance $\sigma^{-2}$ and the prior variance of the basis coefficient vector $\{\lambda_l\}_{l=1}^{L}$ can be given as:

$$\lambda_l^{new} = \frac{\mu_l^2}{1 - \lambda_l^{-1}[\Sigma_b]_{ll}} \quad (18)$$

$$(\sigma^2)^{new} = \frac{\|y - \Gamma\mu\|^2}{L - \sum_{l=1}^{L}(1 - \lambda_l^{-1}[\Sigma_b]_{ll})}.$$

where $\mu_l$ are elements of vector u.

For the EM algorithm, the updating rules for the noise variance $\sigma^{-2}$ and the prior variance $\{\lambda_l\}_{l=1}^{L}$ can be given as:

$$\lambda_l^{new} = [\Sigma_b]_{ll} + \mu_l^2 \quad (19)$$

$$(\sigma^2)^{new} = \frac{\sigma^2 \sum_{l=1}^{L}(1 - \lambda_l^{-1}[\Sigma_b]_{ll}) + \|y - \Gamma\mu\|^2}{M}.$$

In one possible embodiment, the SBL workflow can iterate the estimating stage (Eqns. (11)-(15)) and the updating stage (Eqns. (16)-(19)) until a desired stopping criterion is met.

Figure 6B:
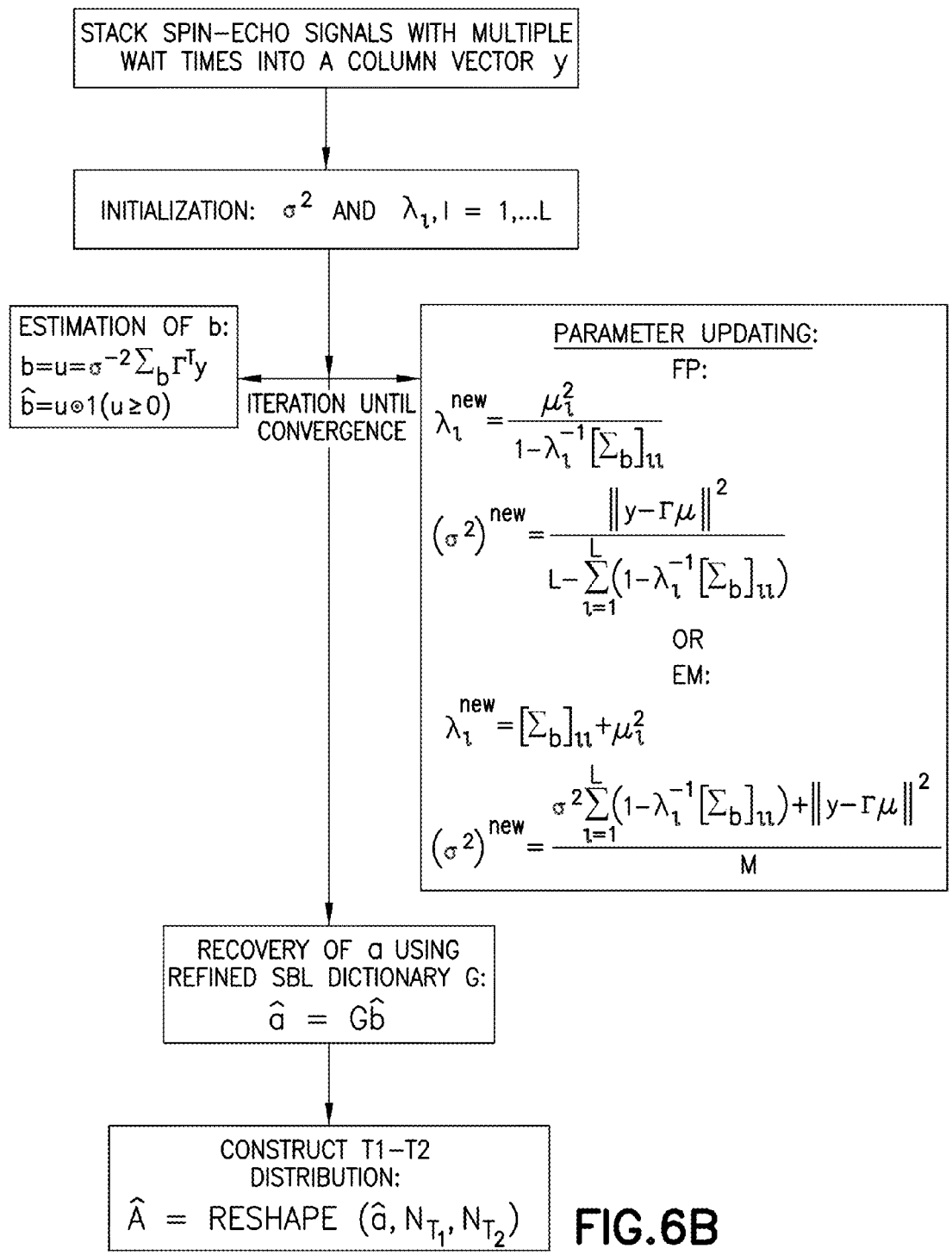
FIG. 6B is an example flowchart for operations that perform sparse Bayesian learning (SBL) as part of the workflow of FIGS. 61A and 6A2.

FIGS. 6A1 and 6A2, collectively, is a flowchart of an example workflow employing sparse Bayesian learning (SBL) to determine a joint $T_1$-$T_2$ distribution.

In block 1001, an initial SBL dictionary is defined and stored in computer memory that is part of (or accessible by) an NMR logging tool (such as the module 132 of the tool shown in FIG. 1). The initial SBL dictionary can be chosen based on SNR or lab studies. For example, the initial SBL dictionary can be designed, learned and trained from prior knowledge, available NMR data, and other measurement logs. In one embodiment, the size of the Gaussian basis of the initial SBL dictionary can be determined or linked to SNR. At high SNR, a refined Gaussian basis may be used to promote resolution; while at low SNR, a larger Gaussian basis can be used for more robust performance. The initial SBL dictionary can also be defined by adaptive methods from clean NMR lab samples.

In one embodiment, the initial SBL dictionary can be a symmetric Gaussian dictionary. The size of the Gaussian basis can be determined or linked to a grid size of the unknown intermediate and final multi-dimensional property distributions (such as the grid size in the $T_1$ and $T_2$ domains) determined in blocks 1011 and 1015 as described below. For example, the standard deviation of a Gaussian basis can be defined as:

$$\sigma = \frac{n_{\Delta T} \Delta T}{\sqrt{2\ln 2}}, \quad (20)$$

where $\sigma$ is the standard deviation or the size of the Gaussian basis, $\Delta T$ is the grid size in the $T_1$ or $T_2$ domain, and $n_{\Delta T}$ is the number of grids in $T_1$ or $T_2$ away from the Gaussian center to decay half of the maximum.

Figure 16C:
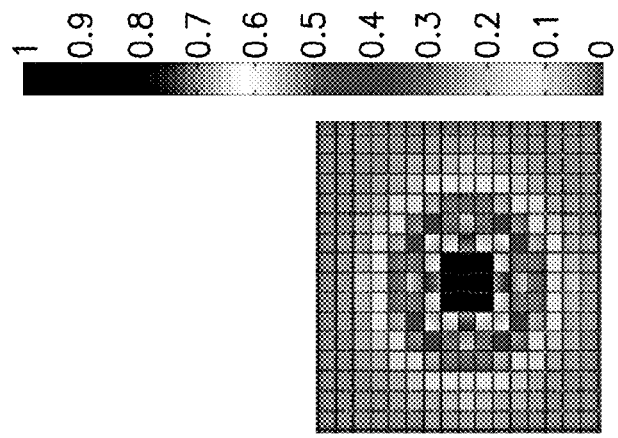
FIGS. 16A, 16B, and 16C are plots that illustrate a number of symmetric Gaussian basis as a function of a number of grids in $T_1$ or $T_2$ away from the Gaussian center to decay half of the maximum ($n_{AT}$).
Figure 16B:
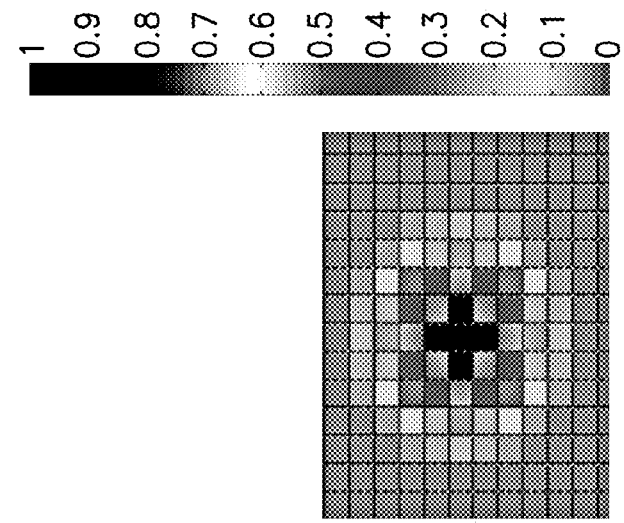
Figure 16A:
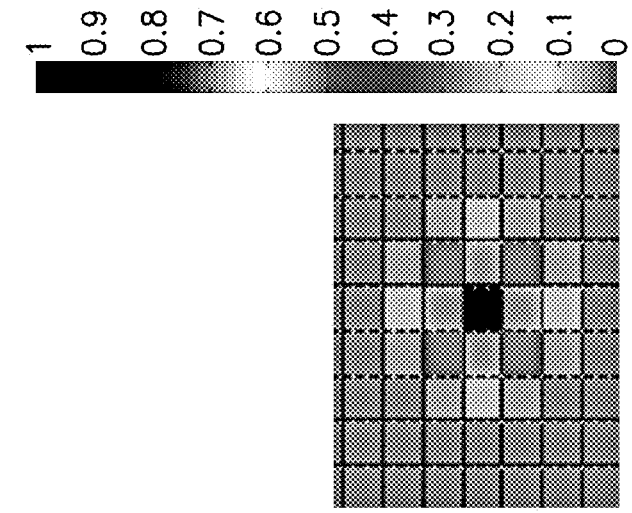
Figure 17C:
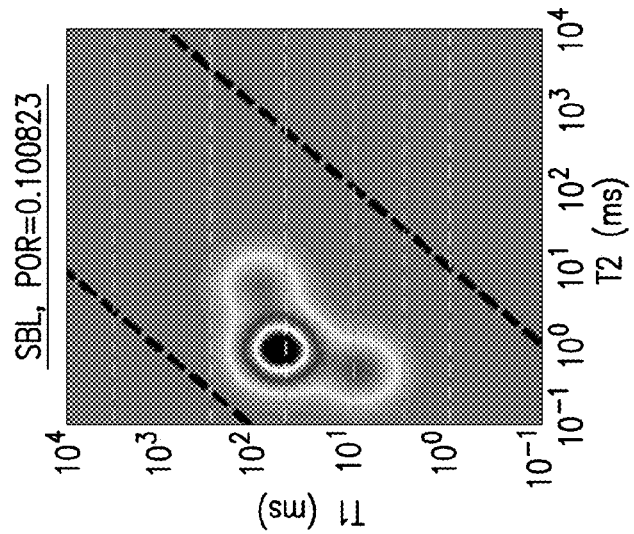
FIGS. 17A, 17B and 17C are T1-T2 maps that illustrate intermediate $T_1$-$T_2$ distributions determined using the symmetric Gaussian basis of FIGS. 16A, 16B and 16C, respectively, as part of an initial SBL dictionary.
Figure 17B:
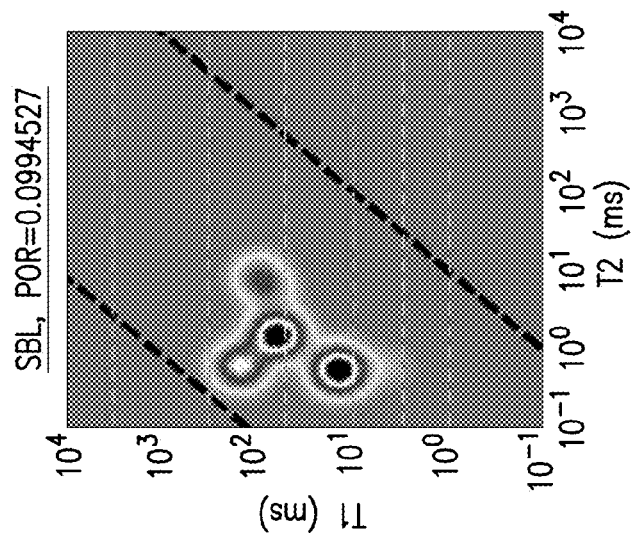
Figure 17A:
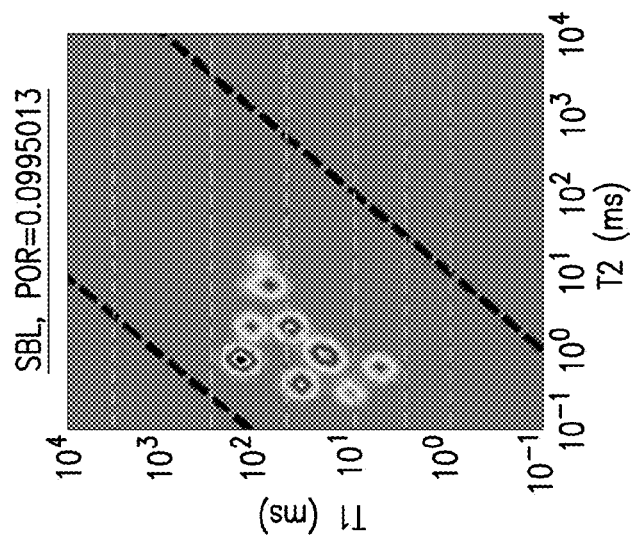

FIGS. 16A, 16B and 16C illustrate a number of symmetric Gaussian basis as a function of $n_{\Delta T}$. FIG. 16A is a plot of a symmetric Gaussian basis where $n_{\Delta T}=1$. FIG. 16B is a plot of a symmetric Gaussian basis where $n_{\Delta T}=2$. FIG. 16C is a plot of a symmetric Gaussian basis where $n_{\Delta T}=3$. The grid size is the same for all three plots. Note that the size of the symmetric Gaussian basis can affect the multi-dimensional property distributions determined in blocks 1011 and 1015 as described below. FIG. 17A is a $T_1$-$T_2$ map that illustrates an intermediate $T_1$-$T_2$ distribution determined in block 1011 as described below using the symmetric Gaussian basis of FIG. 16A as part of the initial SBL dictionary. FIG. 17B is a T1-$T_2$ map that illustrates an intermediate T1-$T_2$ distribution determined in block 1011 as described below using the symmetric Gaussian basis of FIG. 16B as part of the initial SBL dictionary. FIG. 17C is a T1-$T_2$ map that illustrates an intermediate $T_1$-$T_2$ distribution determined in block 1011 as described below using the symmetric Gaussian basis of FIG. 16C as part of the initial SBL dictionary. Note that there are variations amongst the $T_1$-$T_2$ distributions of FIGS. 17A, 17B and 17C as a result of the different sizes in the symmetric Gaussian basis used to derive the $T_1$-$T_2$ distributions.

In block 1003, the NMR logging tool is located at a given depth in a wellbore that traverses a formation for investigating a local region of the formation adjacent the NMR logging tool, and the MR logging tool is configured to perform an NMR experiment (which includes multiple pulse sequences each with a leading wait time) to acquire and store in computer memory NMR data corresponding to the multiple pulse sequences. For example, the NMR experiment can include three CPMG sequences as shown in FIGS. 3A, 3B and 3C with different wait times.

Turning back to FIGS. 6A1 and 6A2, in block 1005, the NMR data of block 1003 can be processed to estimate an initial multi-dimensional property distribution (e.g., initial T1-$T_2$ distribution). Conventional multi-dimensional inversion methodology can be applied to the NMR data of block 1003 to estimate the initial multi-dimensional property distribution. Examples of such conventional multi-dimensional inversion methodology include, for example, the multi-dimensional non-negative Tikhonov regularized least square method and the L1-minimization method.

Figures 18A, 18B, 18C:
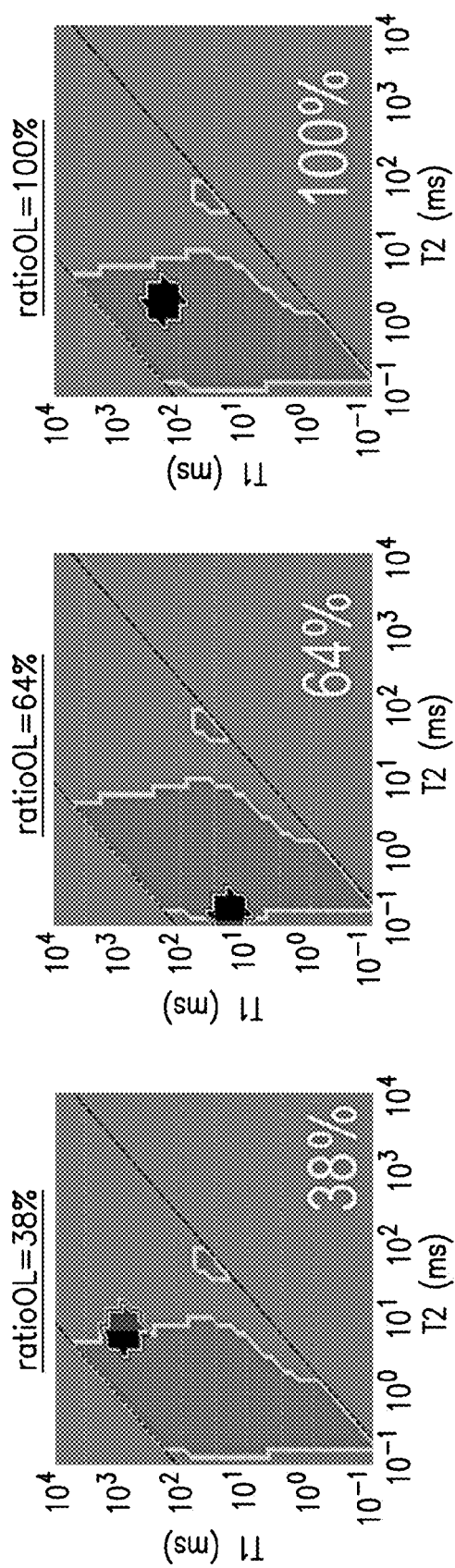
FIGS. 18A, 18B and 18C are plots that illustrate the results of correlation/overlap processing that derives a basis support map for three different basis of an initial SBL dictionary.

In block 1007, the initial multi-dimensional property distribution of block 1005 is used to define a basis support map. The basis support map is a range of multi-dimensional solution space that is estimated to support the unknown intermediate and final multi-dimensional property distributions determined in blocks 1011 and 1015 as described below. The basis support map can be derived by computing a correlation or overlap between the initial multi-dimensional property distribution of block 1005 and the corresponding basis of the initial SBL dictionary of block 1001 for each grid point of the multi-dimensional solution space (e.g., $T_1$, $T_2$ grid points. FIGS. 18A, 18B and 18C are plots that illustrate the results of such correlation/overlap processing for three different basis of the initial SBL dictionary of block 1001. When this correlation is above a predefined threshold (e.g., 20%) for a given grid point, the value of the basis support map for the given grid point is set to a value (such as "1") that indicates that the corresponding basis of the initial SBL dictionary of block 1001 should be included in the refined dictionary (in block 1009). When this correlation is below the predefined threshold for the given grid point, the value of the basis support map for the given grid point is set to a value (such as "0") that indicates that the corresponding basis of the initial SBL dictionary of block 1001 should be excluded from the refined dictionary (in block 1009); instead the refined dictionary employs a null or "0" basis for the given grid point.

Figure 19:
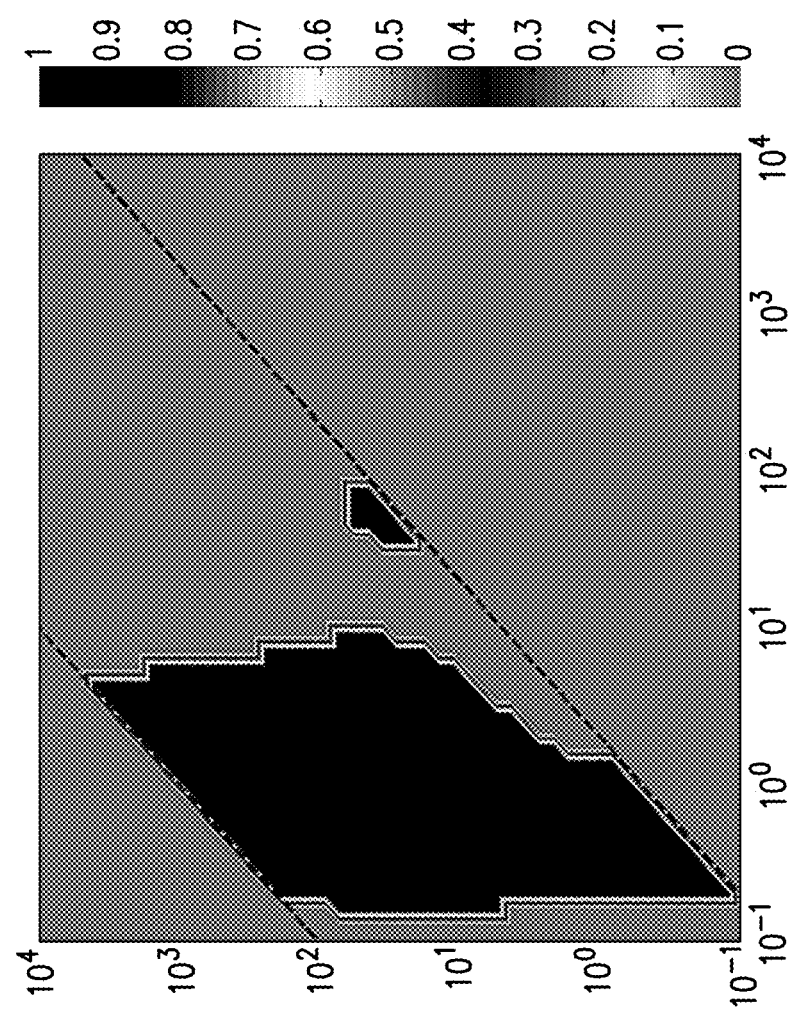
FIG. 19 is a plot that illustrates an example basis support map.

FIG. 19 is a plot of an example basis support map. In this plot, the darker colored area(s) are grid points having a basis support map value (such as "1") that indicates that the corresponding basis of the initial SBL dictionary of block 1001 should be included in the refined dictionary (in block 1009), while the lighter colored area(s) are grid points having a basis support map value (such as "0") that indicates that the corresponding basis of the initial SBL dictionary of block 1001 should be excluded from the refined dictionary (in block 1009) (instead, the refined dictionary employs a null or "0" basis for the given grid point).

Turning back to FIGS. 6A1 and 6A2, in block 1009, the values of the basis support map of block 1007 are used to refine the initial SBL dictionary of block 1001 to produce a refined SBL dictionary. For example, the respective basis of the initial SBL dictionary can be by selectively included or excluded based on the values of the basis support map for the grid points of the multi-dimensional solution space as determined in block 1007. When the respective basis of the initial SBL dictionary is excluded, the refined dictionary can employ a null or "0" basis for the given grid point. The refined SBL dictionary can be stored computer memory for subsequent processing.

In block 1011, the NMR data of block 1003 can be processed using SBL learning with the refined SBL dictionary of block 1009 to determine an intermediate multi-dimensional property distribution (e.g., a $T_1$-$T_2$ distribution) for the local region of the formation. Details of example SBL learning methodology suitable for block 1011 are illustrated in the flow chart of 6B.

Figure 20C:
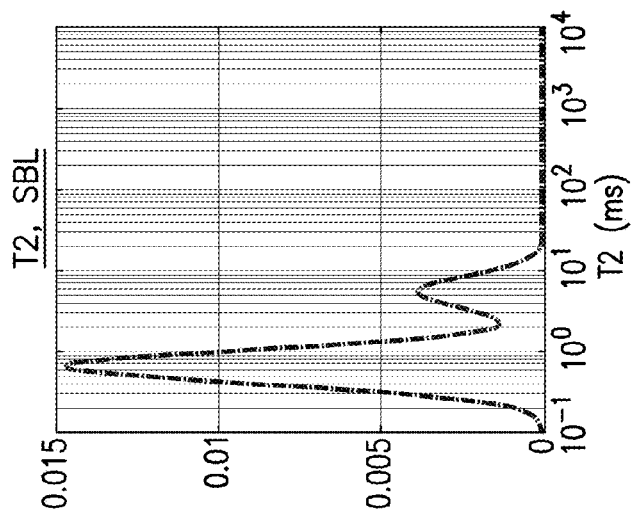
FIGS. 20A, 20B and 20C are plots that illustrate an example intermediate T1-$T_2$ distribution using SBL learning with a refined SBL dictionary.
Figure 20B:
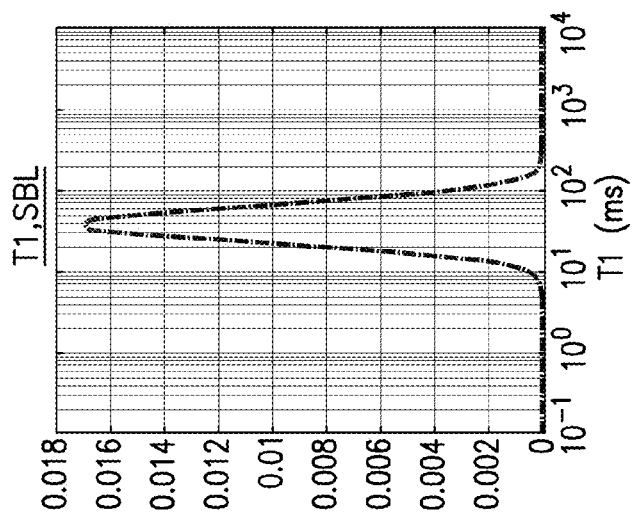
Figure 20A:
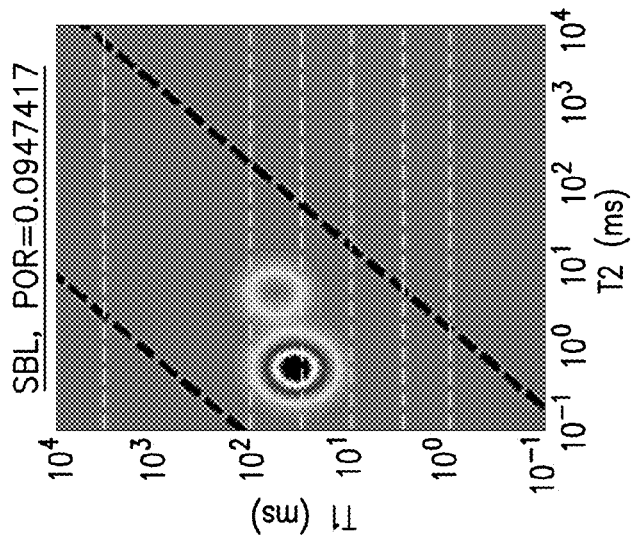

FIGS. 20A, 20B and 20C are plots that illustrate an example intermediate T1-T2 distribution as determined in block 1011 using SBL learning with the refined SBL dictionary of block 1009. FIG. 20A is a $T_1$-$T_2$ plot of the example intermediate $T_1$-$T_2$ distribution. FIG. 20B is a plot of the $T_1$ distribution that makes up the example intermediate $T_1$-$T_2$ distribution. FIG. 20C is a plot of the $T_2$ distribution that makes up the example intermediate $T_1$-$T_2$ distribution.

Turning back to FIGS. 6A1 and 6A2, in block 1013, the intermediate multi-dimensional property distribution of block 1011 can be stored in computer memory for subsequent processing.

In block 1015, Monte-Carlo resampling can be used to evaluate uncertainty in the intermediate multi-dimensional property distribution stored in block 1013 and update the intermediate multi-dimensional property distribution to determine a final multi-dimensional property distribution.

In block 1017, the final multi-dimensional property distribution (e.g., final T1-$T_2$ distribution) of block 1015 can be stored in computer memory for output and evaluation of the local region of the formation.

In block 1019, the operations determine whether the NMR logging tool will be relocated to another depth of the well for NMR logging at that depth. If so, the operations return to block 1003 to repeat the logging at the next depth. If not, the NMR logging operations end.

Figure 6C:
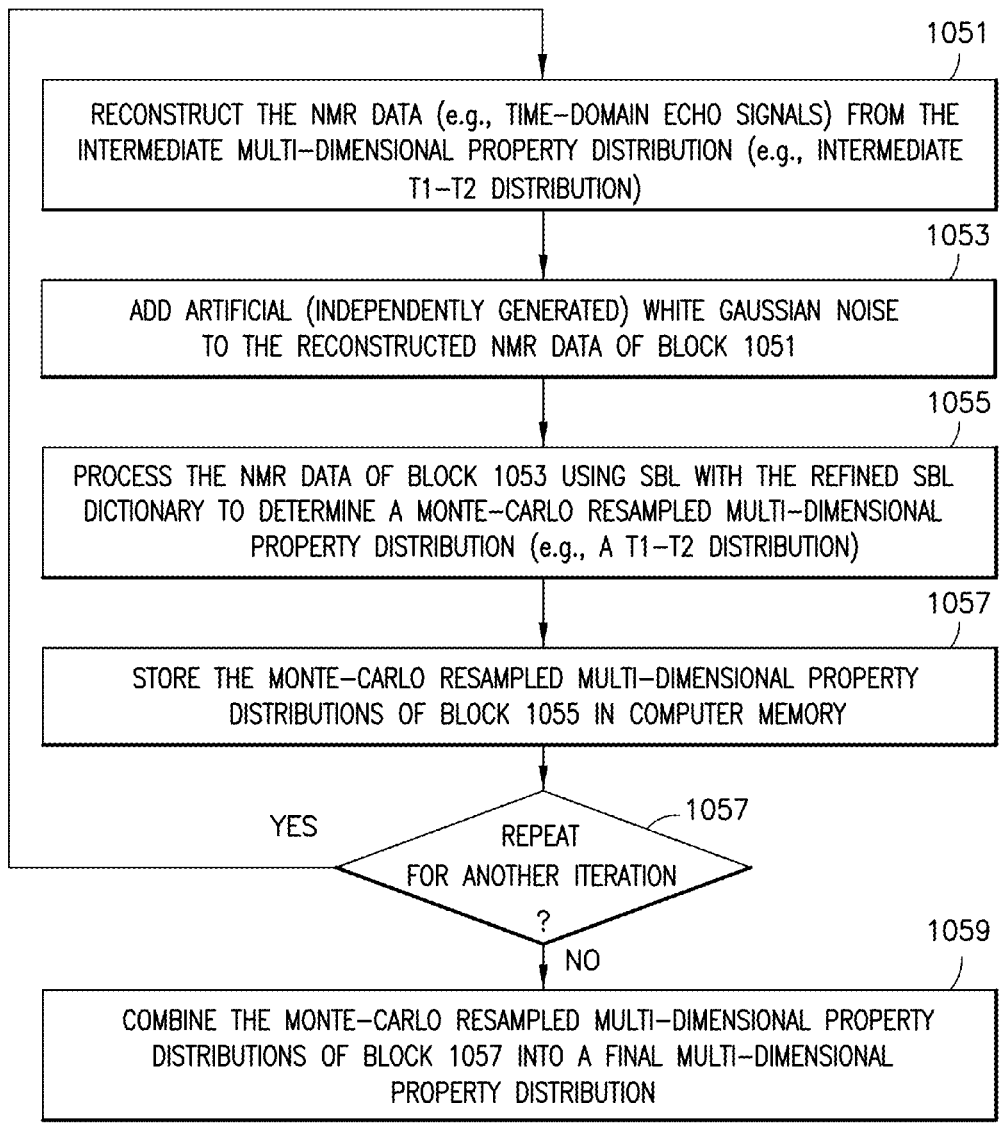
FIG. 6C is an example flowchart for operations that perform Monte-Carlo resampling of an intermediate multi-dimensional property distribution of NMR data as part of the workflow of FIGS. 61A and 6A2.

FIG. 6C illustrates an embodiment of the Monte-Carlo resampling of the intermediate multi-dimensional property distribution of block 1015.

Such operations begin in block 1051 where NMR data (e.g., time-domain echo signals) is reconstructed from the intermediate multi-dimensional property distribution (e.g., intermediate $T_1$-$T_2$ distribution). Such reconstruction can be based on a forward model, such as the signal model of Eqn. (1) set forth above.

FIGS. 21A, 21B and 21C are plots that illustrate an example intermediate T1-$T_2$ distribution using SBL learning with a refined SBL dictionary. FIG. 21A is a $T_1$-$T_2$ plot of the example intermediate $T_1$-$T_2$ distribution. FIG. 21B is a plot of the $T_1$ distribution that makes up the example intermediate $T_1$-$T_2$ distribution. FIG. 21C is a plot of the $T_2$ distribution that makes up the example intermediate $T_1$-$T_2$ distribution.

Figure 22:
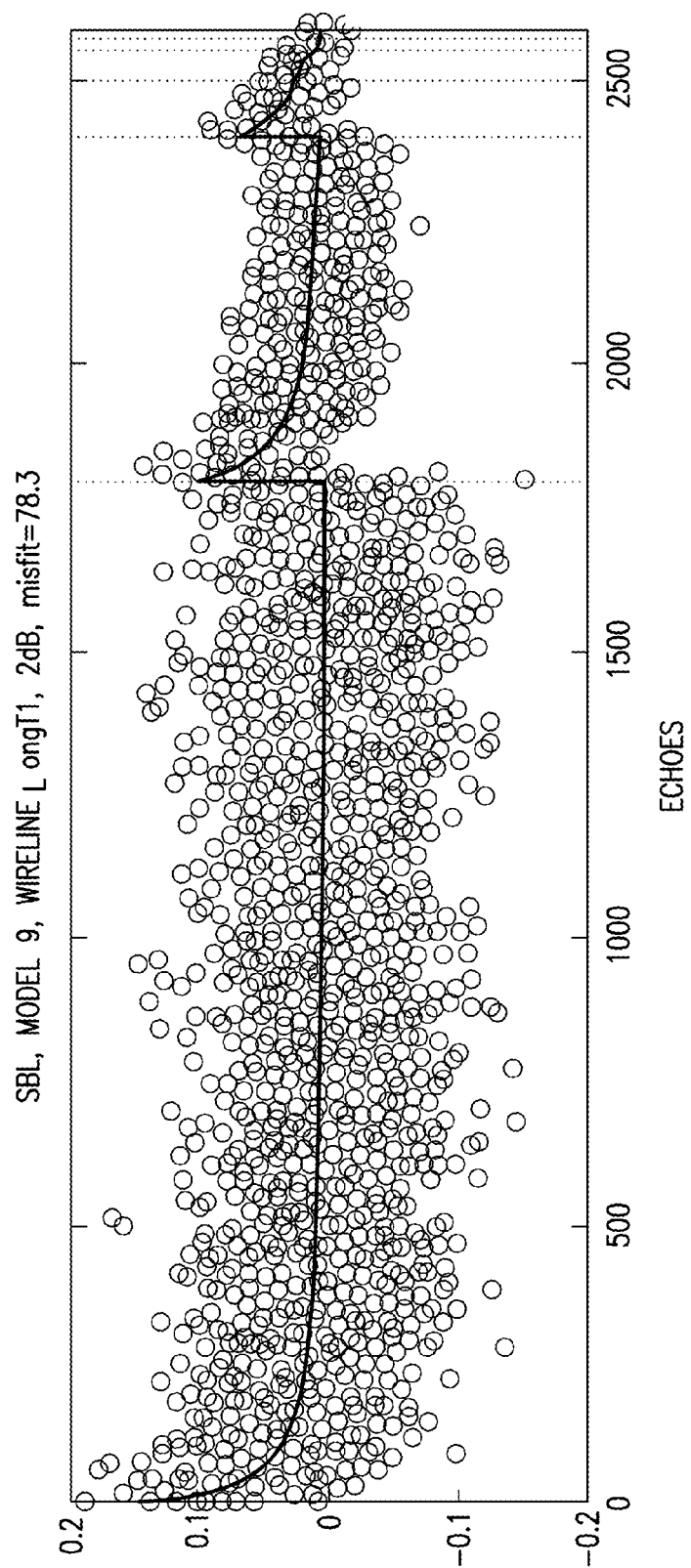
FIG. 22 shows an example of reconstructed NMR data reconstructed from the example intermediate T1-$T_2$ distribution of FIGS. 21A, 21B and 21C.

FIG. 22 shows an example of reconstructed NMR data reconstructed from the example intermediate $T_1$-$T_2$ distribution of FIGS. 21A, 21B and 21C. FIG. 22 shows the reconstructed NMR data in the solid curve along with the measured raw NMR data (which was obtained in block 1003) in circles.

Turning back to FIG. 6C, in block 1053, artificial (independently generated) white Gaussian noise can be added to the reconstructed NMR data of block 1051.

In block 1055, the NMR data of block 1053 (with added artificial noise) can be processing using SBL with the refined SBL dictionary to determine a Monte-Carlo resampled multi-dimensional property distribution (e.g., a $T_1$-$T_2$ distribution). Such operations are similar to block 1011. Details of example SBL methodology suitable for block 1055 are illustrated in the flow chart of 6B.

In block 1057, the Monte-Carlo resampled multi-dimensional property distribution of block 1055 can be stored in computer memory.

The Monte-Carlo resampling operations of blocks 1053 to 1507 can be repeated for a number of iterations with different realizations of noise added to the NMR data in block 1053. Block 1059 checks whether all of the iterations have been completed. If not, the operations revert to block 1053 to repeat the operations of blocks 1053 to 1057 for the next iteration. If so, the operations continue to block 1059.

In block 1059, the Monte-Carlo resampled multi-dimensional property distributions stored in block 1057 for the number of iterations of the Monte-Carlo resampling are combined to produce the final multi-dimensional property distribution. In one example, the final multi-dimensional property distribution can be derived from the mean of all Monte-Carlo resampled multi-dimensional property distributions stored in block 1057 for the number of iterations of the Monte-Carlo resampling.

Figures 23, 23A:
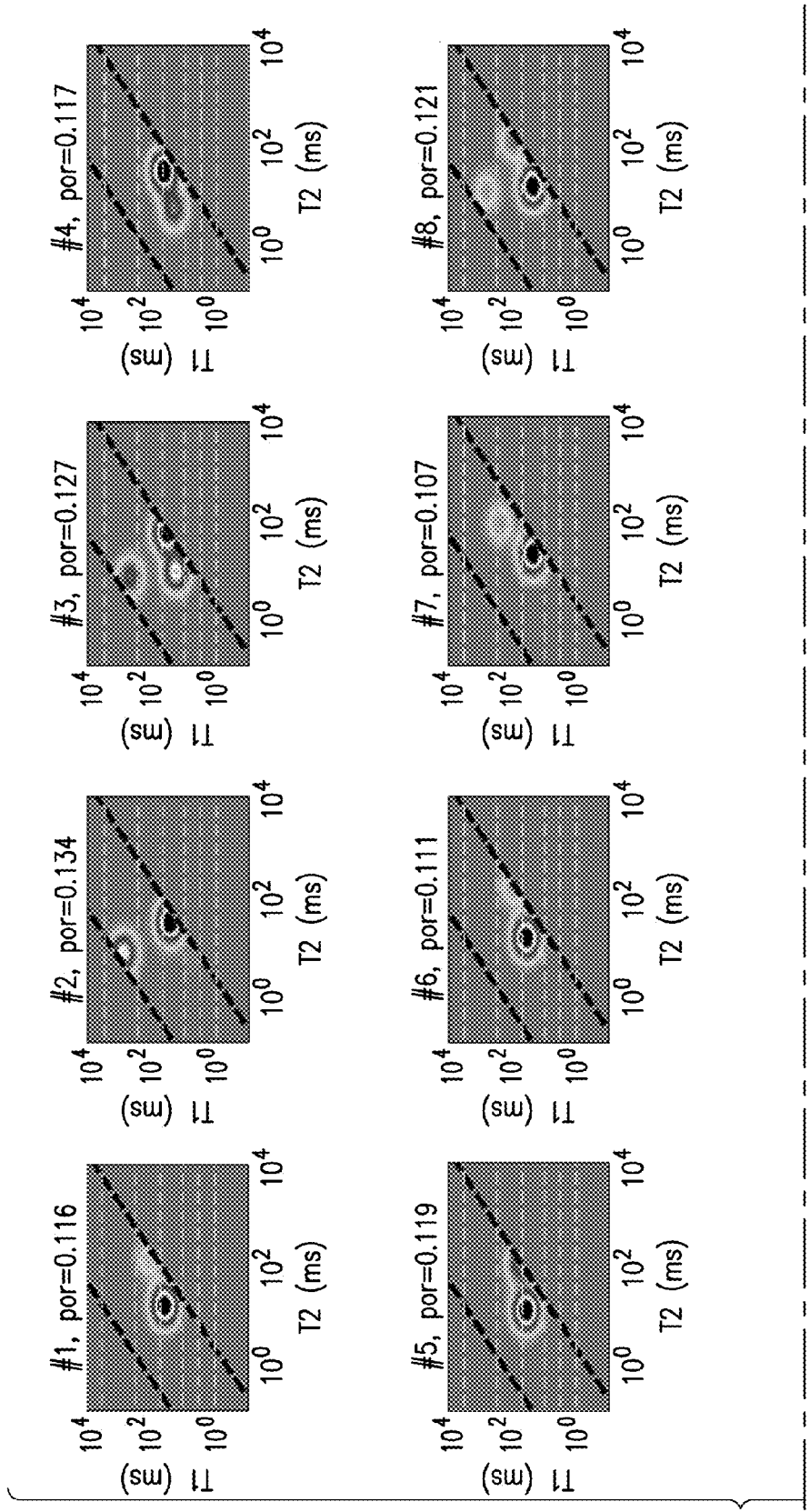
FIGS. 23 (23a and 23b) shows sixteen Monte-Carlo resampled multi-dimensional property distributions generated and stored for sixteen iterations of resampling operations with different realizations of noise added to NMR data.
Figure 23B:
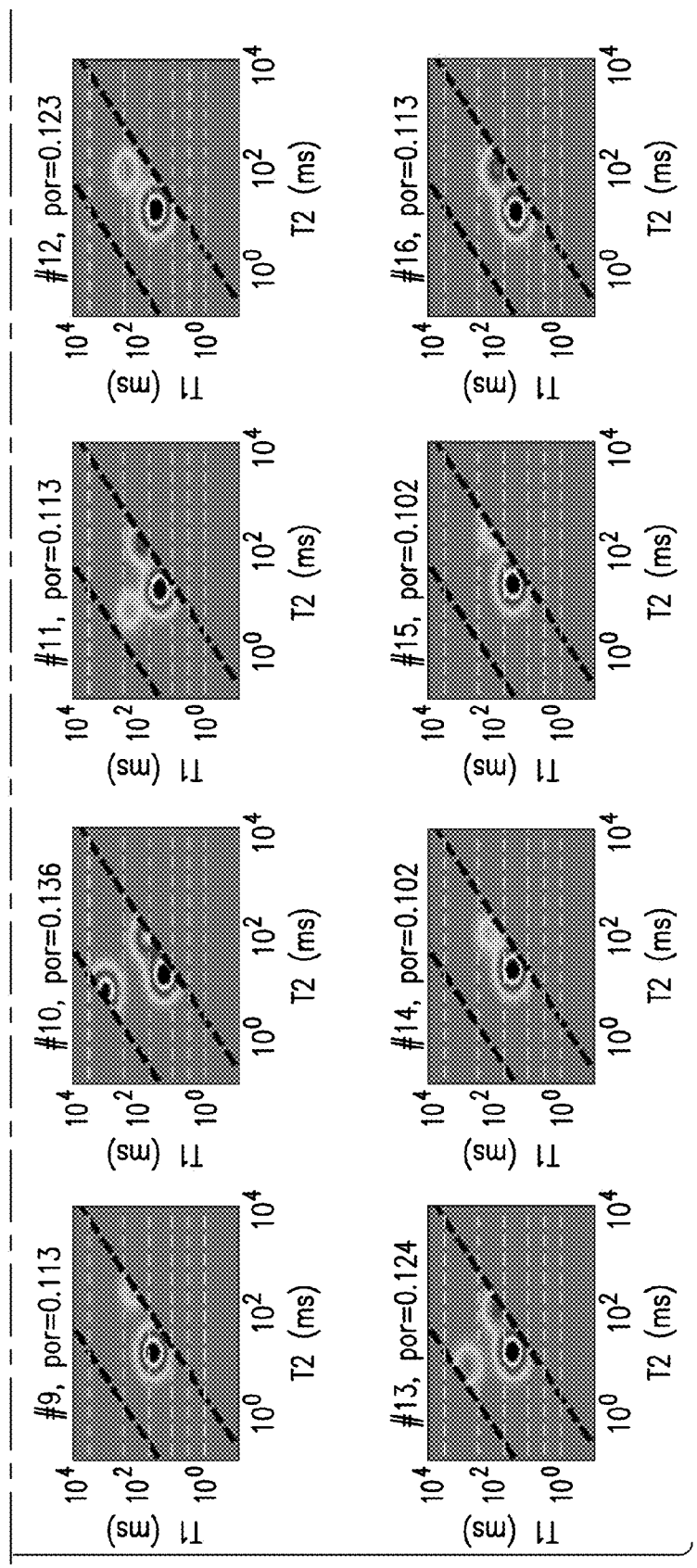

FIG. 23 shows sixteen Monte-Carlo resampled multi-dimensional property distributions generated in block 1055 and stored in block 1057 for sixteen iterations of the resampling operations of blocks 1053 to 1057 with different realizations of noise added to NMR data in block 1053.

Figure 24A:
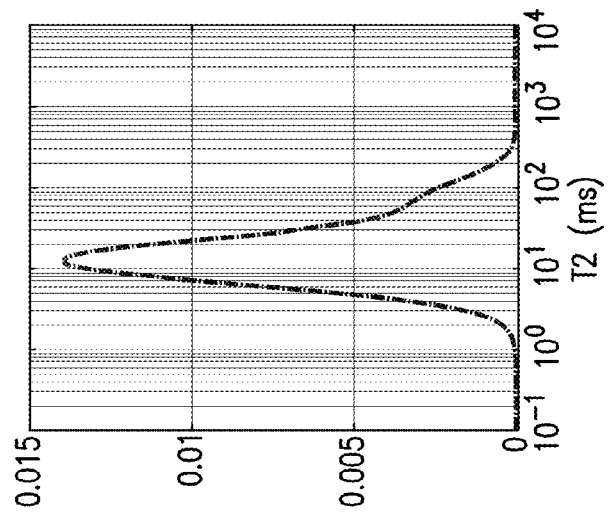
FIGS. 24A, 24B and 24C are plots that illustrate an example final T1-$T_2$ distribution determined by combining the sixteen Monte-Carlo resampled T1-$T_2$ distributions of FIG. 23.
Figure 24B:
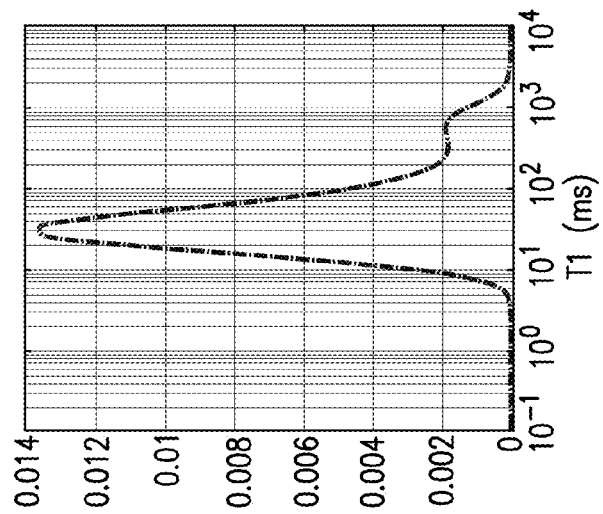
Figure 24C:
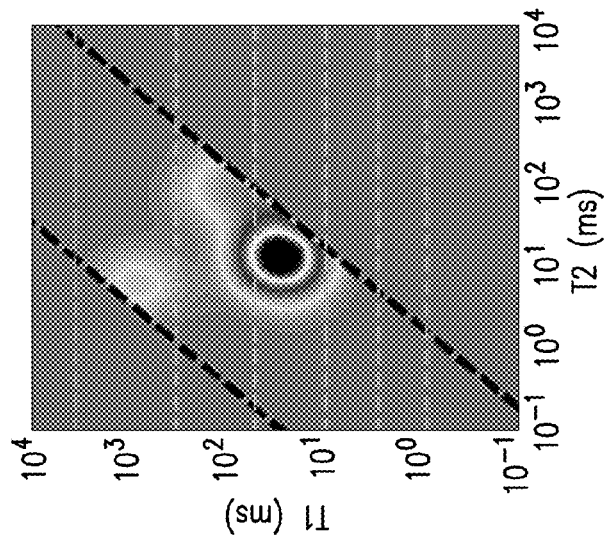

FIGS. 24A, 24B and 24C are plots that illustrate an example final $T_1$-$T_2$ distribution as determined in block 1057 by combining the sixteen Monte-Carlo resampled $T_1$-$T_2$ distributions of FIG. 23. FIG. 24A is a $T_1$-$T_2$ plot of the example final $T_1$-$T_2$ distribution. FIG. 24B is a plot of the $T_1$ distribution that makes up the example final $T_1$-$T_2$ distribution. FIG. 24C is a plot of the $T_2$ distribution that makes up the example final $T_1$-$T_2$ distribution.

Example Results

In one possible embodiment, the results of a proposed workflow can be illustrated through use of a synthetic dataset.

Figure 7A:
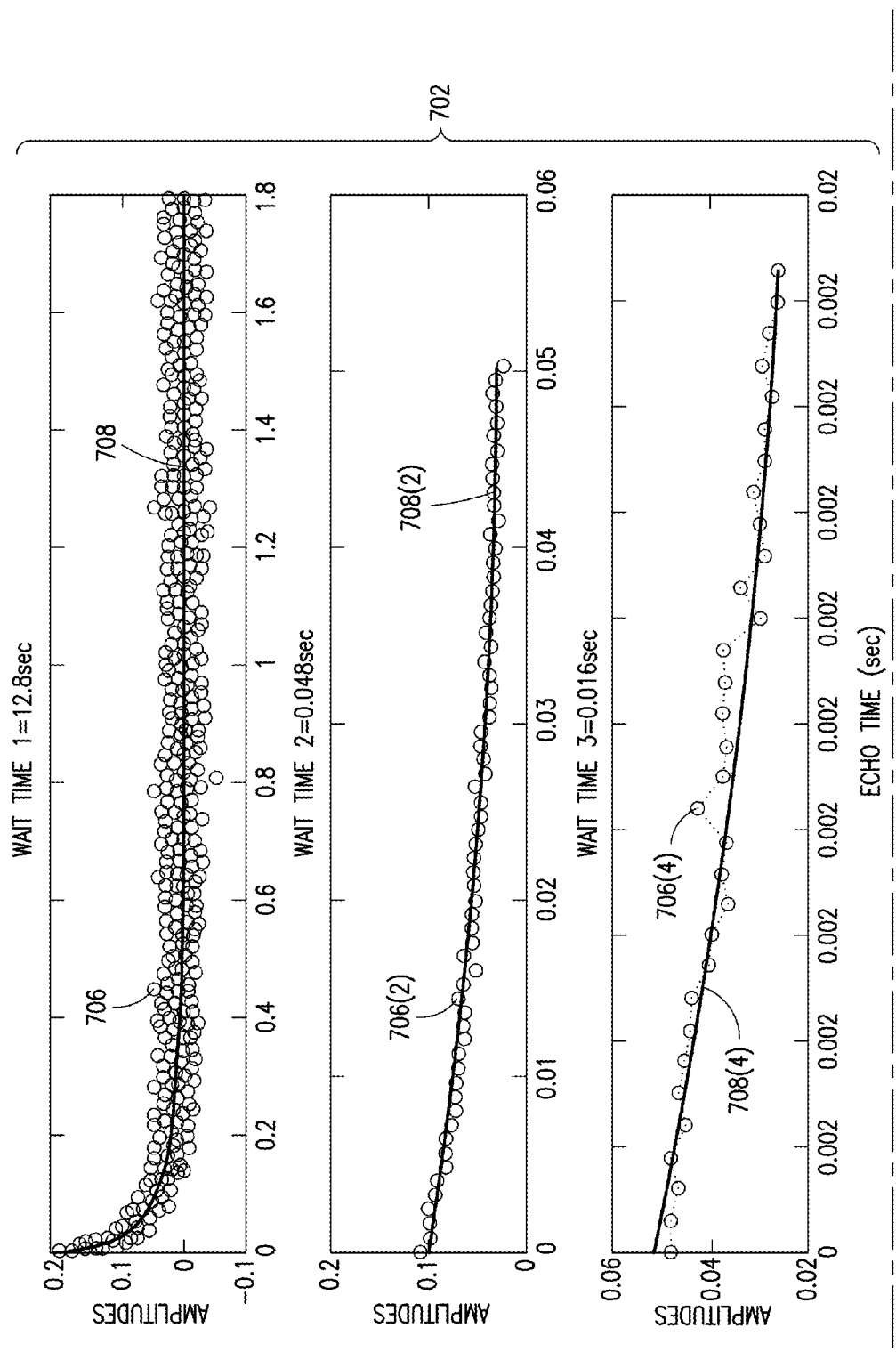
FIGS. 7 (7a and 7b) illustrates example spin-echo amplitudes corresponding to three wait times in accordance with various embodiments of the present disclosure.

FIG. 7 illustrates example spin-echo amplitudes corresponding to three wait times in accordance with certain implementations of NMR measurement processing. As illustrated, spin-echo amplitudes corresponding to three wait times ([WT1, WT2, WT3]=[12.8, 0.048, 0.016] in seconds (s) are given for raw samples 702 and windowed samples 704. In both plots 702, 704, circles 706 denote the noisy samples while curves 708 denote the noiseless synthetic signal. The window interval functions are [1,1,1,1,1,1,14, 28,112,160,640,540] for WT1, [1,1,1,1,1,1,14,44] for WT2, and [1,1,1,1,1,1,8,18] for WT3.

In one possible embodiment, the number of wait times in (1) can be 1=3. The numbers of echoes can be [$M_1$, $M_2$, $M_3$]=[1500, 64, 32] with corresponding echo spacing [$\Delta t_1$, $\Delta t_2$, $\Delta t_3$]=[1.2, 0.8, 0.6] in millisecond (ms), and the wait times can be [$WT_1$ $WT_2$ $WT_2$]=[12.8, 0.048, 0.016] in seconds(s). For the second and third wait times, 32 and 64 repetitions, for example, can be recorded to improve the signal-to-noise ratio. With the above experimental setting, the length of the overall measurement vector y in Eqn. (1) is 1596. In practice, these 1596 measurements can be compressed into a short vector by a windowing operation; that is a summation of the original measurements over a local time window can be conducted. In this example as well as the next lab data example, a number of window functions can be used for the three wait-time measurements as follows:

$$[\text{win}(WT_1)] = [1\ 1\ 1\ 1\ 1\ 1\ 14\ 28\ 112\ 160\ 640\ 540]$$
$$[\text{win}(WT_2)] = [1\ 1\ 1\ 1\ 1\ 1\ 14\ 44]$$
$$[\text{win}(WT_3)] = [1\ 1\ 1\ 1\ 1\ 1\ 8\ 18]$$

The windowed samples are shown in plots 704.

Figure 8:
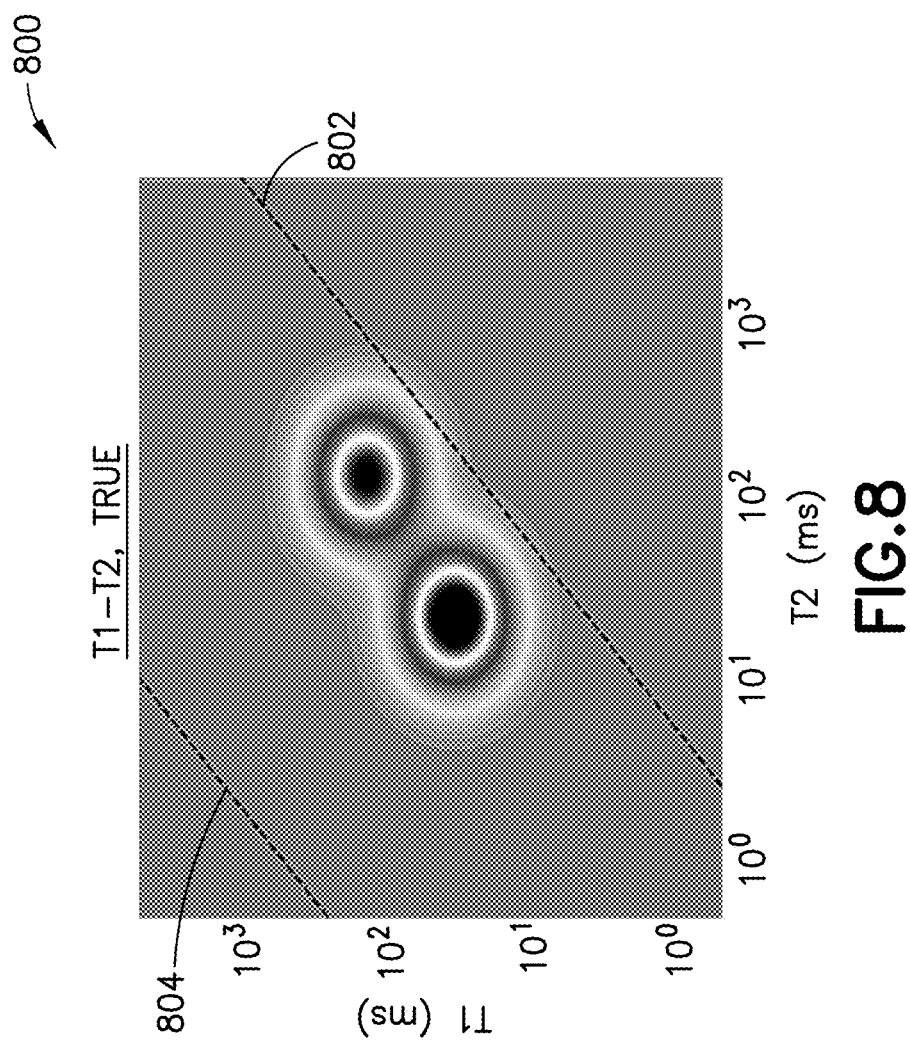
FIG. 8 illustrates an example true $T_1$-$T_2$ distribution used to synthesize the noiseless model NMR measurement in accordance with various embodiments of the present disclosure.

FIG. 8 illustrates an example true $T_1$-$T_2$ distribution 800 used to synthesize the noiseless model NMR measurement as denoted as curves 708 in plots 702. The range of $T_1$ and $T_2$ is approximately from 1 to 1000 s. The dash lines 802, 804 in FIG. 8 represent assumed minimum and maximum $T_1/T_2$ ratios.

Figure 9:
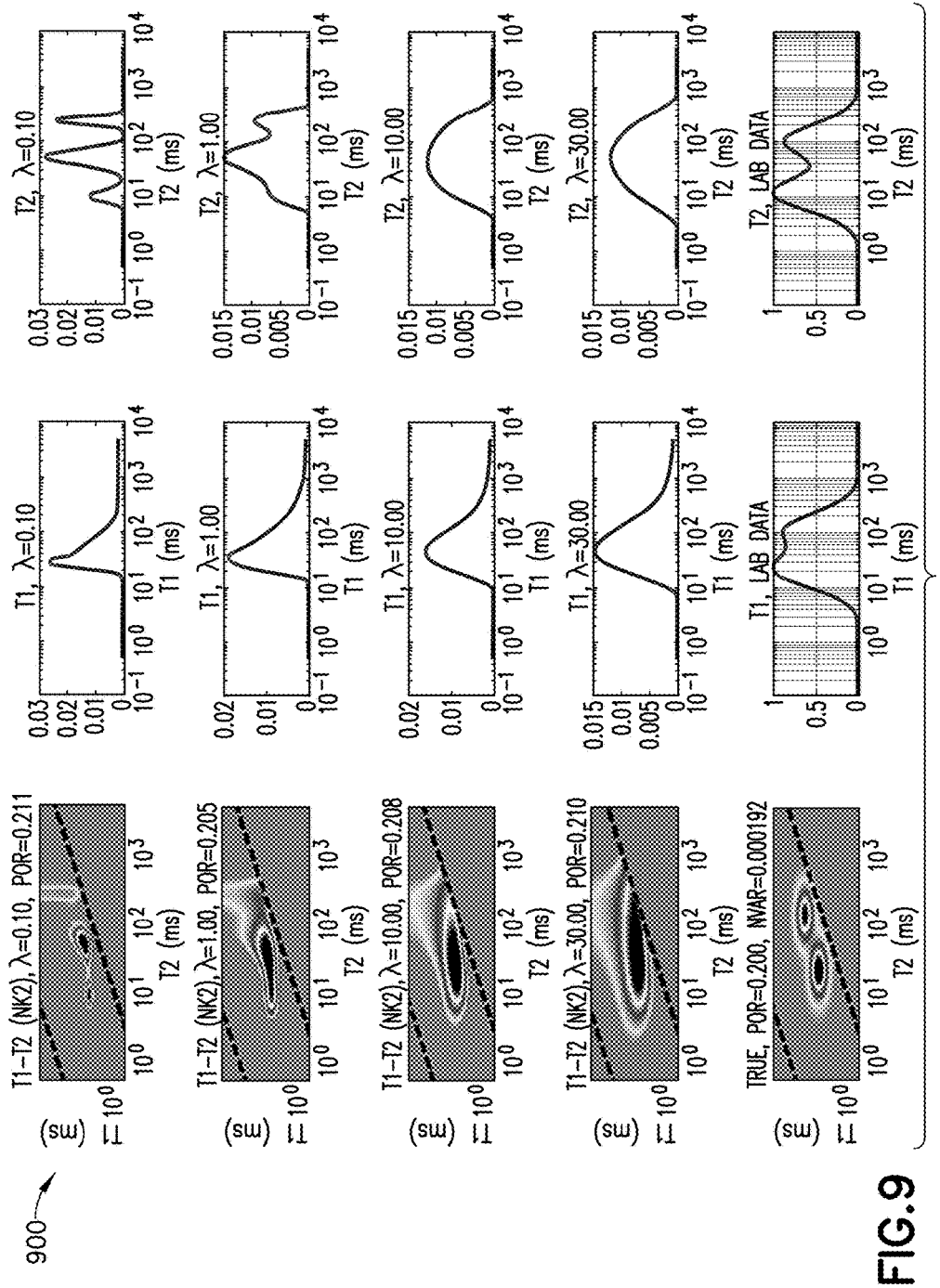
FIG. 9 illustrates an example initial $T_1$-$T_2$ distribution inverted from NMR data in accordance with various embodiments of the present disclosure.

FIG. 9 shows an example inverted $T_1$-$T_2$ distribution 900 by using the non-negative Tikhonov regularized least square method (denoted as NK2 in plots) with several choices of regularization parameters. The last row 902 represents the true $T_1$-$T_2$ distribution, and $T_1$ and $T_2$ spectra, respectively. In one possible embodiment, it can be seen that the result interpretations are dependent on the chosen regularization parameter. In one possible embodiment, this dependence can become more evident when the measurements become noisy. For example, in this method, without exploring the Gaussian support in the $T_1$-$T_2$ domain, difficulties may be encountered in resolving the two active $T_1$-$T_2$ regions.

Figure 10:
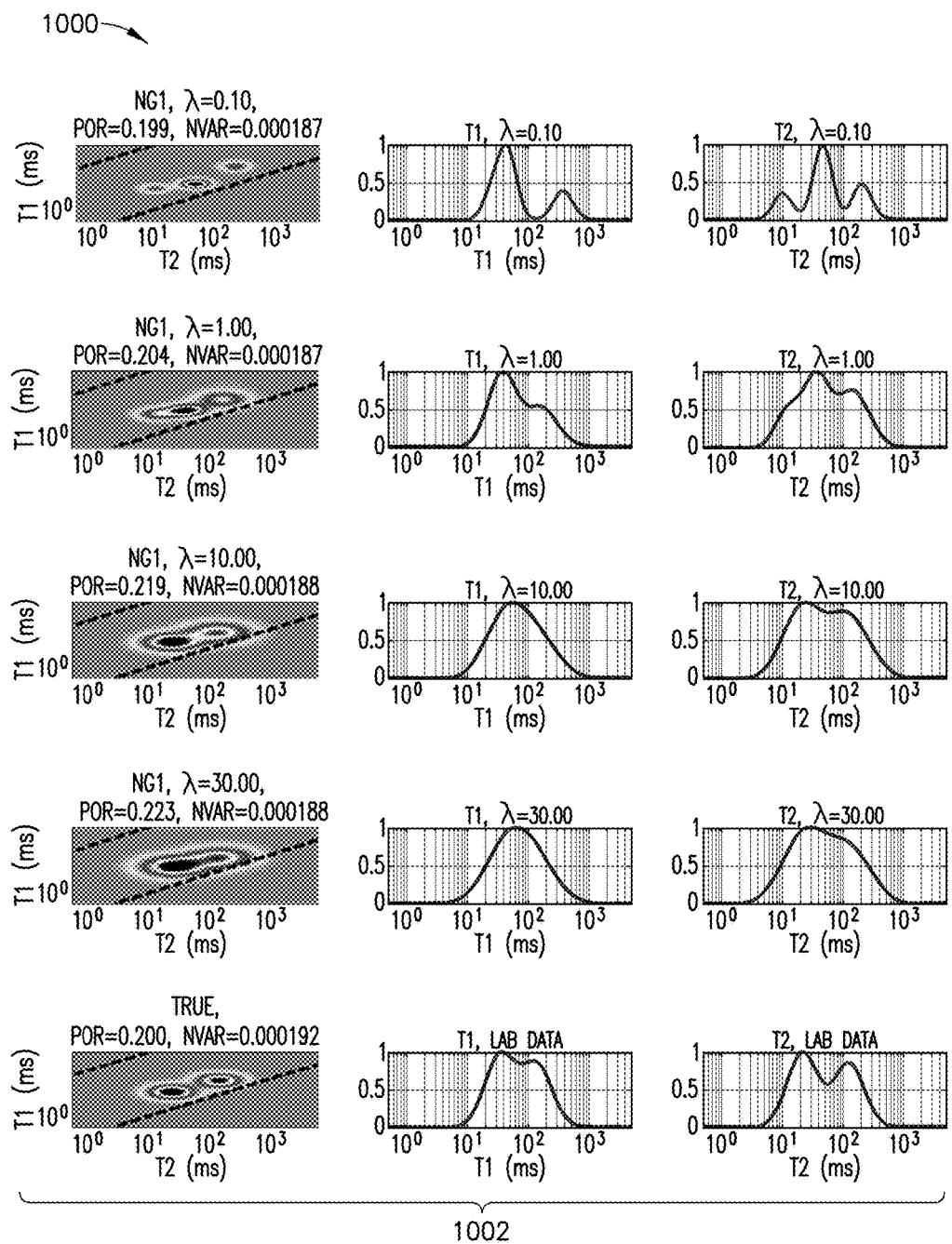
FIG. 10 illustrates an example initial $T_1$-$T_2$ distribution inverted from NMR data in accordance with various embodiments of the present disclosure.

FIG. 10 illustrates an example inverted $T_1$-$T_2$ distribution 100 by using the non-negative $L_1$-minimization (denoted as NG1 in plots) with several choices of regularization parameters. In one possible embodiment, the last row 1002 represents the true $T_1$-$T_2$ distribution, and $T_1$ and $T_2$ spectra, respectively.

In one possible embodiment, the inversion results may be dependent on the chosen regularization parameter. Comparing FIG. 10 with FIG. 9 it can be seen that the $L_1$-minimization method, while exploring the Gaussian support in the $T_1$-$T_2$ domain, can start to resolve the two active $T_1$-$T_2$ regions with a regularization parameter, for example, $\lambda=1$.

Figure 11:
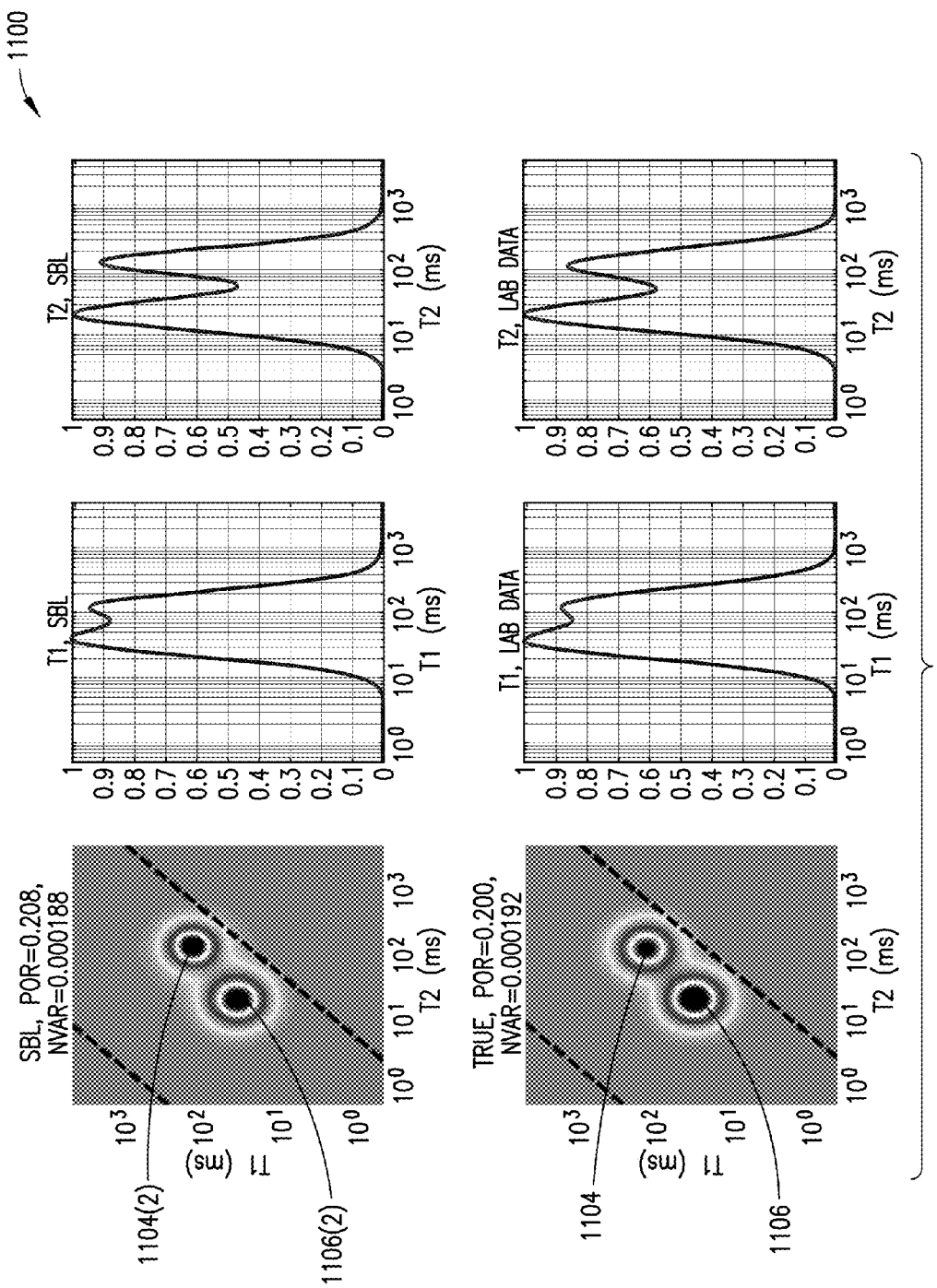
FIG. 11 illustrates an example intermediate $T_1$-$T_2$ distribution inverted from NMR data in accordance with various embodiments of the present disclosure.

FIG. 11 shows an example inverted $T_1$-$T_2$ distribution 1100 by using the proposed workflow without manually selecting the regularization parameter/method. In one possible embodiment, this automated workflow can deliver results with decreased and/or minimal dependence on the regularization parameter. The last row 1102 represents the true $T_1$-$T_2$ distribution, and $T_1$ and $T_2$ spectra, respectively. In addition, the inversion results in FIG. 11 show two resolved $T_1$-$T_2$ regions 1104, 1106, which were not fully seen in FIG. 9 and FIG. 10.

To further evaluate the performance of the above mentioned methods, in one possible implementation, Monte-Carlo simulations can be run by varying the noise level and the number of measurements (including, for example, the wait time). In one possible embodiment, for a given simulation scenario, the Monte-Carlo simulation can perform, for example, 50 independent runs with independently generated noise in each run.

Figure 12:
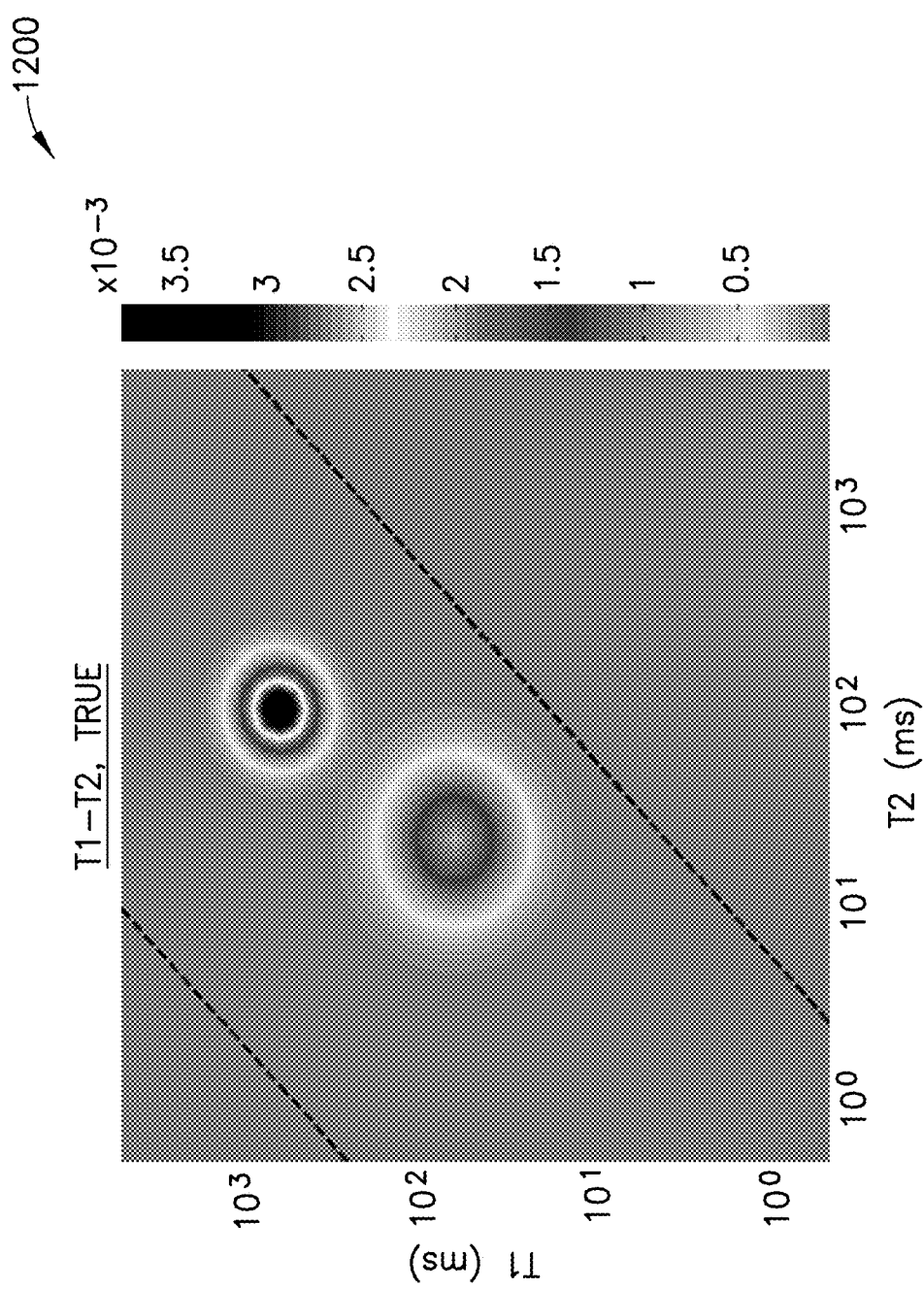
FIG. 12 illustrates an example true $T_1$-$T_2$ distribution in accordance with various embodiments of the present disclosure.

FIG. 12 illustrates an example true $T_1$-$T_2$ distribution 1200, used for waveform generation in the Monte-Carlo evaluation, which is discretized in a 50-by-50 logarithmically equally spaced grid in the $T_1$ and $T_2$ domains, respectively.

In one possible embodiment, a simulation scenario can be used with, for example, 5 wait times at [12.800, 1.000, 0.150, 0.048, 0.016] in second(s). In one possible aspect, the number of echoes can be [M1, M2, M3, M4, M5]=[800, 160, 120, 64, 32] with corresponding echo spacing [1.2, 1.0, 0.8, 0.6, 0.4] in milliseconds (ms) and repetition counts [1, 1, 4, 32, 64].

Figure 13A:
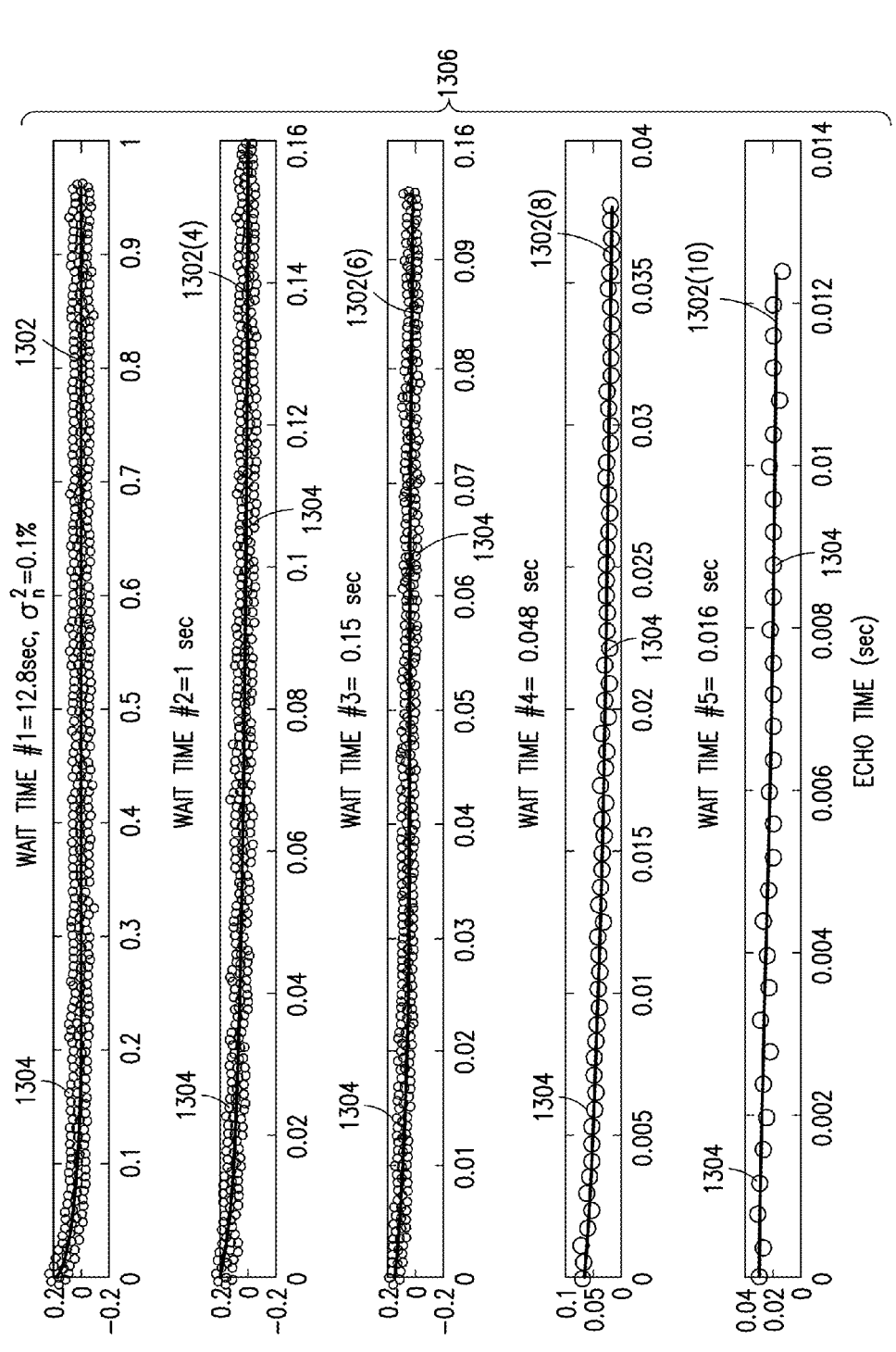
FIGS. 13 (13a and 13b) illustrates example synthetic signals with $T_1$-$T_2$ distributions in accordance with various embodiments of the present disclosure.
Figure 13B:
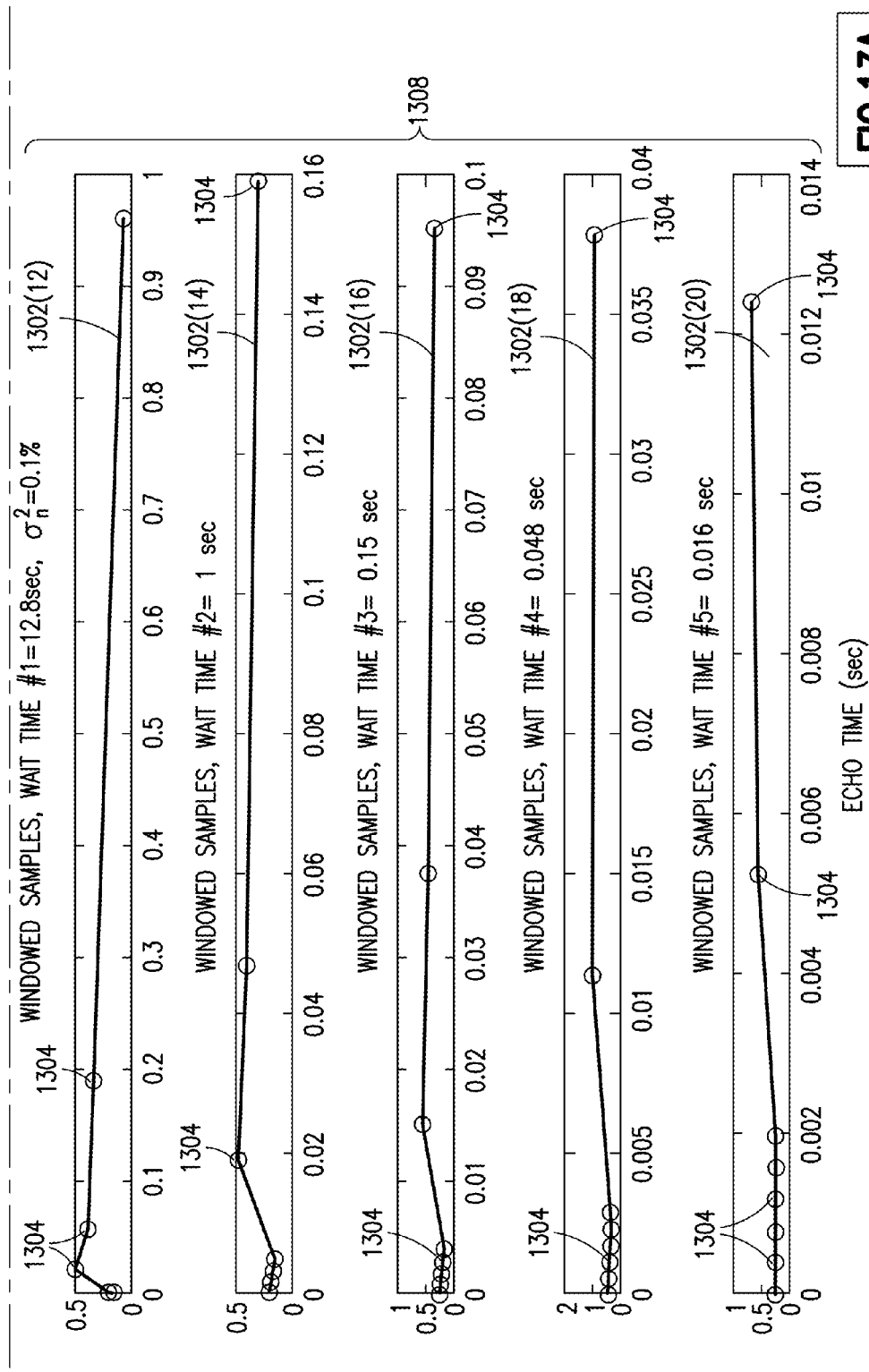

FIG. 13 illustrates the synthetic signal with the $T_1$-$T_2$ distribution in FIG. 12 and the above configuration parameters in curves 1302. In one possible embodiment, the noise with variance equal to 0.1% of the total porosity can be added to the synthetic signal in each Monte-Carlo simulation. Circles 1304 in plots 1306 show one-realization of such additive noise. Plots 1306 illustrate raw samples. The windowed (compressed) signals are shown in plots 1308.

In one possible embodiment, circles 1304 denote noisy samples while curves 1302 denote noiseless signals. The noise variance is 0.1% of the high value of signal at time 0 (which is also the total porosity).

FIGS. 14A1 to 14C2 illustrate example $T_1$ and $T_2$ results found by integrating corresponding T1-$T_2$ distributions derived from the methods discussed herein. FIGS. 14A1 and 14A2 illustrate example $T_1$ and $T_2$ results found by integrating an initial $T_1$-$T_2$ distribution inverted from NMR data in accordance with various embodiments of the present disclosure. FIGS. 14B1 and 14B2 illustrate example $T_1$ and $T_2$ results found by integrating an initial $T_1$-$T_2$ distribution inverted from NMR data in accordance with various embodiments of the present disclosure. FIGS. 14C1 and 14C2 illustrate example $T_1$ and $T_2$ results found by integrating an intermediate $T_1$-$T_2$ distribution inverted from NMR data in accordance with various embodiments of the present disclosure. The curves 1402 denote the T1 and $T_2$ results integrated from corresponding $T_1$-$T_2$ distributions from the 50 Monte-Carlo runs and curves 1404 denote the true $T_1$ and $T_2$ results integrated from the true T1-$T_2$ distribution of FIG. 12. From the results, it is seen that, compared with previous results with 3 wait times, the non-negative Tikhonov regularized least square method (NK2) shows capability to separate the two peaks in both $T_1$ and $T_2$ domain with 5 wait times. Nevertheless, the sparsity-regularized $L_1$-minimization (NG1) and SBL methods show improved resolution in the $T_1$ domain and improved estimation coherence in the $T_2$ domain. The noise variance is 0.1% of the total porosity.

FIGS. 15A1 to 15C2 illustrate example $T_1$ and $T_2$ results found by integrating corresponding $T_1$-$T_2$ distributions inverted from simulation results when a Monte-Carlo simulation is repeated with 3 wait times (as in FIG. 7) in accordance with various embodiments of the present disclosure. In this case, the non-negative Tikhonov regularized least square method (NK2) with the regularization parameter $\lambda=1$ cannot resolve the two peaks in the $T_1$ domain. As compared with the NK2 method, the $L_1$-minimization (NG1) method with the regularization parameter $\lambda=1$ can separate the two peaks in the $T_1$ domain with a higher probability. By adaptively selecting the regularization parameter of sparsity from the data, the various methods described above appear to have the highest probability to recover the two peaks in the $T_1$ domain. Specifically, FIGS. 15A1 and 15A2 illustrate example $T_1$ and $T_2$ results found by integrating an initial $T_1$-$T_2$ distribution inverted from simulation results when a Monte-Carlo simulation is repeated with 3 wait times in accordance with various embodiments of the present disclosure. FIGS. 15B1 and 15B2 illustrate example $T_1$ and $T_2$ results found by integrating an initial $T_1$-$T_2$ distribution inverted from simulation results when a Monte-Carlo simulation is repeated with 3 wait in accordance with various embodiments of the present disclosure. FIGS. 15C1 and 15C2 illustrate example $T_1$ and $T_2$ results found by integrating an intermediate $T_1$-$T_2$ distribution inverted from simulation results when a Monte-Carlo simulation is repeated with 3 wait times in accordance with various embodiments of the present disclosure. The curves 1502 denote the $T_1$ and $T_2$ results integrated from the corresponding $T_1$-$T_2$ distributions and curves 1504 denote the true $T_1$ and $T_2$ results integrated from the true $T_1$-$T_2$ distribution of FIG. 12. The noise variance is 0.1% of the total porosity.

Note that the inversion methodology and workflow as described herein can be adapted to acquire and process wellbore nuclear magnetic resonance (NMR) measurements at different depths of investigation with the downhole NMR tool located at a particular depth or location within a well in order to characterize the different depths of investigation into the subterranean formation at the particular depth or location within the well. In this case, the wellbore nuclear magnetic resonance (NMR) measurements can be carried out over several RF frequencies in order to measure (image) multiple sample volumes at different depths of investigation with the downhole NMR tool located at the particular depth or location within the well.

Also note that the inversion methodology and workflow as described herein is no limited to downhole NMR applications. For example, the inversion methodology and workflow as described herein can be used to analyze NMR data of formation samples (such as rock core samples or loaded with formation fluid) captured by a laboratory NMR system in a laboratory setting.

Although a few example embodiments have been described in detail above, those skilled in the art will readily appreciate that many modifications are possible in the example embodiments without materially departing from this disclosure. Accordingly, such modifications are intended to be included within the scope of this disclosure.

The invention claimed is:

1. A method of characterizing a subterranean formation, the method comprising:
   locating a downhole logging tool in a wellbore that traverses the subterranean formation;
   performing nuclear magnetic resonance (NMR) measurements using the downhole logging tool to obtain NMR data for a region of the subterranean formation adjacent the downhole logging tool; and
   processing the NMR data by employing sparse Bayesian learning (SBL) to determine a multi-dimensional property distribution that characterizes the region of the subterranean formation adjacent the downhole logging tool;
   wherein the sparse Bayesian learning recovers a vector of basis coefficients from a vector representing the NMR data and a matrix representing the product of a kernel matrix and a dictionary matrix, wherein the dictionary matrix is derived from an estimated multi-dimensional property distribution of the NMR data.

2. A method according to claim 1, wherein:
   the performing NMR measurements comprises obtaining NMR data for different depths of investigation into the subterranean formation at a particular location in the well bore; and
   the processing of the obtained NMR data is adapted to determine multi-dimensional property distributions that characterize the different depths of investigations into the subterranean formation at the particular location in the well bore.

3. A method according to claim 1, wherein:
   the performing NMR measurements comprises obtaining NMR data for regions of the subterranean formation at different locations in the wellbore; and
   the processing of the obtained NMR data is adapted to determine multi-dimensional property distributions that characterize the regions of the subterranean formation at different locations in the wellbore.

4. A method according to claim 1, wherein the multi-dimensional property distribution comprises at least one of T1-T2, D-T2, and D-T1-T2 distributions, where T1 is a longitudinal-relaxation time, T2 is a transverse-relaxation time, and D is a diffusion coefficient.

5. A method according to claim 1, wherein the dictionary matrix includes a linear combination of basis elements.

6. A method according to claim 5, wherein the dictionary matrix comprises an overcomplete Gaussian dictionary.

7. A method according to claim 5, wherein the dictionary matrix comprises a structural matrix.

8. A method according to claim 7, wherein the structural matrix comprises at least one of a two-dimensional Gaussian support matrix, a two-dimensional ellipse matrix, and a two-dimensional wavelet matrix.

9. A method according to claim 1, wherein the sparse Bayesian learning utilizes Bayesian inference that involves a prior distribution over the vector of basis coefficients governed by a set of hyperparameters, one associated with each basis coefficient, whose values are iteratively estimated from the NMR data.

10. A method according to claim 1, wherein the sparse Bayesian learning achieves sparsity because posterior distributions of many of such basis coefficients are sharply peaked around zero.

11. A method according to claim 1, wherein the sparse Bayesian learning recovers the vector of basis coefficients further from a noise variance and a prior variance.

12. A method according to claim 11, wherein:
the sparse Bayesian learning recovers the vector of basis coefficients by iteratively processing first and second stages;
the first stage deriving a posterior distribution of the vector of basis coefficients assuming the prior variance and noise variance are known; and
the second stage employing rules for updating the noise variance and the prior variance.

13. A method according to claim 12, wherein the iterative processing of the first and second stages terminates when a stopping criterion is satisfied.

14. A method according to claim 1, wherein the dictionary matrix comprises a refined dictionary derived from an initial dictionary.

15. A method according to claim 14, wherein:
the initial dictionary is chosen based on signal-to-noise ratio (SNR) or lab studies;
size of the initial dictionary is determined or linked to SNR; and
size of the initial dictionary is determined or linked to a grid size of yet unknown multi-dimensional property distributions.

16. A method according to claim 14, wherein the refined dictionary is determined by:
deriving the estimated multi-dimensional property distribution of the NMR data, correlating the estimated multi-dimensional property distribution of the NMR data to the initial dictionary to derive a basis support map, and using the basis support map to update the initial dictionary to form the refined dictionary.

17. A method according to claim 16, wherein:
the correlating is performed over grid points of the estimated multi-dimensional property distribution of the NMR data; and
the basis support map includes values that indicate whether the basis of the initial dictionary corresponding to a respective grid point should be part of the refined dictionary.

18. A method according to claim 1, wherein:
the NMR data is processed by sparse Bayesian learning (SBL) to determine an intermediate multi-dimensional property distribution of the NMR data; and
Monte-Carlo resampling is used to evaluate uncertainty in the intermediate multidimensional property distribution and update the intermediate multi-dimensional property distribution to determine a final multidimensional property distribution.

19. A method according to claim 18, wherein:
the Monte-Carlo resampling includes a number of iterations each involving (i) reconstructing the NMR data from the intermediate multi-dimensional property distribution, (ii) adding artificial white Gaussian noise to the reconstructed NMR data, and (iii) processing the NMR data using sparse Bayesian learning (SBL) to determine a Monte-Carlo resampled multi-dimensional property distribution.

20. A method according to claim 19, wherein the Monte-Carlo resampling further includes combining the Monte-Carlo resampled multi-dimensional property distribution for the number of iterations to form the final multidimensional property distribution.

21. A method according to claim 1, wherein the NMR data is obtained from an experiment involving a number of pulse sequences with corresponding wait times.

22. A system for characterizing a subterranean formation, the system comprising:
a nuclear magnetic resonance (NMR) logging tool configured (i) to be located within a wellbore that traverses the subterranean formation and (ii) to perform NMR measurements of a region of the subterranean formation adjacent the NMR logging tool to obtain NMR data; and
an NMR processing module configured to process the NMR data by employing sparse Bayesian learning (SBL) to determine a multi-dimensional property distribution of the NMR data;
wherein the sparse Bayesian learning recovers a vector of basis coefficients from a vector representing the NMR data and a matrix representing the product of a kernel matrix and a dictionary matrix, wherein the dictionary matrix is derived from an estimated multi-dimensional property distribution of the NMR data.

23. A system for characterizing a formation sample, the system comprising:
a laboratory nuclear magnetic resonance (NMR) tool configured to perform NMR measurements on a formation sample to obtain NMR data; and
an NMR processing module configured to process the NMR data by employing sparse Bayesian learning (SBL) to determine a multi-dimensional property distribution of the NMR data;
wherein the sparse Bayesian learning recovers a vector of basis coefficients from a vector representing the NMR data and a matrix representing the product of a kernel matrix and a dictionary matrix, wherein the dictionary matrix is derived from an estimated multi-dimensional property distribution of the NMR data.

* * * * *